(12) United States Patent
Weber et al.

(10) Patent No.: US 8,227,653 B2
(45) Date of Patent: Jul. 24, 2012

(54) OLEFIN OLIGOMERIZATION REACTION PROCESSES EXHIBITING REDUCED FOULING

(75) Inventors: Michael W. Weber, Humble, TX (US); James R. Lattner, LaPorte, TX (US); Laughlin G. McCullough, League City, TX (US); Randell W. Dickey, Baytown, TX (US); Steven D. Brown, League City, TX (US); Peter N. Loezos, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/203,590

(22) PCT Filed: Mar. 27, 2009

(86) PCT No.: PCT/US2009/038609
§ 371 (c)(1),
(2), (4) Date: Oct. 3, 2011

(87) PCT Pub. No.: WO2010/110801
PCT Pub. Date: Sep. 30, 2010

(65) Prior Publication Data
US 2012/0016097 A1    Jan. 19, 2012

(51) Int. Cl.
  *C07C 2/08*    (2006.01)
  *C08F 2/00*    (2006.01)
  *C08F 210/02*  (2006.01)
(52) U.S. Cl. ............ 585/527; 585/520; 585/950; 526/75
(58) Field of Classification Search ............ 585/527, 585/950, 520; 526/75
See application file for complete search history.

(56) References Cited

U.S. PATENT DOCUMENTS

| | | |
|---|---|---|
| 5,382,738 A | 1/1995 | Reagen et al. |
| 5,451,645 A | 9/1995 | Reagen et al. |
| 5,523,507 A | 6/1996 | Reagen et al. |
| 5,543,375 A | 8/1996 | Lashier et al. |
| 5,637,660 A | 6/1997 | Nagy et al. |
| 5,750,817 A * | 5/1998 | Tanaka et al. ............ 585/520 |
| 6,103,657 A | 8/2000 | Murray |
| 6,380,451 B1 | 4/2002 | Kreischer et al. |
| 6,706,829 B2 | 3/2004 | Boussie et al. |
| 6,713,577 B2 | 3/2004 | Boussie et al. |
| 6,727,361 B2 | 4/2004 | LaPointe et al. |
| 6,750,345 B2 | 6/2004 | Boussie et al. |
| 6,828,397 B2 | 12/2004 | Boussie et al. |
| 7,414,006 B2 | 8/2008 | McConville et al. |
| 7,423,661 B2 | 9/2008 | Abe et al. |
| 7,638,670 B2 | 12/2009 | McConville et al. |
| 7,638,671 B2 | 12/2009 | McConville et al. |
| 7,687,672 B2 | 3/2010 | Buchanan et al. |
| 7,858,833 B2 | 12/2010 | Buchanan et al. |
| 2006/0247483 A1 | 11/2006 | McConville et al. |
| 2007/0185362 A1 | 8/2007 | Lattner et al. |
| 2008/0241095 A1 | 10/2008 | Syrinek |
| 2009/0082573 A1 | 3/2009 | Hagadorn et al. |

FOREIGN PATENT DOCUMENTS

| | | |
|---|---|---|
| EP | 0 230 983 | 8/1987 |
| EP | 0 668 106 | 8/1995 |
| WO | 99/19280 | 4/1999 |
| WO | 2004/056478 | 7/2004 |
| WO | 2004/056479 | 7/2004 |

OTHER PUBLICATIONS

Dixon et al., "*Advances in Selective Ethylene Trimerisation—A Critical Overview*", Journal of Organometallic Chemistry, 2004, vol. 689, pp. 3641-3668.
Robertson et al., "*Chromium(II) and Chromium(III) Complexes Supported by Tris(2-Pyridylmethyl)Amine: Synthesis, Structures, and Reactivity*", Inorganic Chemistry, 2003, vol. 42, pp. 6876-6885.

* cited by examiner

Primary Examiner — Fred M Teskin

(57) ABSTRACT

The invention relates to olefin oligomerization methods and methods for reducing/inhibiting fouling in olefin oligomerization reactions comprising: contacting, in an oligomerization reactor (e.g., under oligomerization conditions), an alpha-olefin feed, a catalyst having an olefin selectivity of at least 90 mol % to a desired oligomerization product, a polymer anti-foulant, and optionally a diluent; selectively producing an effluent comprising the desired oligomerization product, unreacted olefin, and alpha-olefin-based polymer byproduct that causes fouling. The amount of polymer anti-foulant can be chosen to limit fouling to ≦20 g/kg desired oligomerization product, to remediate ≧3 grams fouled polymer/kg desired oligomerization product, and/or to reduce/inhibit polymer fouling by ≧10% over a selective oligomerization with substantially no added polymer anti-foulant. Advantageously, desired oligomerization product so obtained can also be polymerized/copolymerized with an alpha-olefin such as ethylene.

17 Claims, No Drawings

OLEFIN OLIGOMERIZATION REACTION PROCESSES EXHIBITING REDUCED FOULING

This application is a National Stage Application of International Application No. PCT/US2009/38609 filed Mar. 27, 2009, which is hereby incorporated by reference in its entirety.

FIELD OF THE INVENTION

The invention relates to methods for oligomerizing olefins so as to effectively limit polymer byproduct fouling, to remediate already fouled polymer byproduct, or both, simply by adding polymer anti-foulant particles (e.g., that can be similar to the polymer byproduct foulant).

BACKGROUND OF THE INVENTION

Olefin polymerization, especially ethylene polymerization, can benefit from the addition of longer-chain comonomers, such as 1-butene, 1-hexene, and 1-octene, to produce linear low density polyethylene (LLDPE). LLDPE produced from 1-butene, 1-hexene and 1-octene accounts for a large percentage of the polyethylene resin market. In general, polyethylene plants buy butene, hexene and octene, which are produced in separate plants that typically produce a range of even-numbered alpha olefins from ethylene. It can be expensive to purchase these materials, and they add to the complexity of transport, storage and handling. An attractive alternative is to make the comonomer directly from the ethylene at the site where they will be used, if this can be done cleanly and economically.

The review article "Advances in selective ethylene trimerisation—a critical review" by Dixon et al. (*J. Organometallic Chemistry* 689 (2004) 3641-3668), herein incorporated by reference in its entirety, describes many different catalysts for trimerization. These catalyst systems contain chromium, and with particular ligands, such as aromatic species (e.g., pyrrolyl) or multidentate heteroatomic species. The chromium catalysts are typically activated by alkylaluminum and/or alkyaluminoxane activators. The article also describes Groups 4 and 5 early transition metals, such as Zr, V, Ta and Ti, and Group 8 late transition metals, such as Ni, for showing some activity in trimerization.

Phillips has developed chromium-based catalysts that are selective towards making 1-hexene from ethylene. The major byproduct appears to be 1-decene. U.S. Publication No. 2004/0228775 and U.S. Pat. No. 6,380,451, describe a standalone process for making 1-hexene.

U.S. Pat. No. 5,382,738 discloses catalyst systems comprising inorganic oxides, modified with a metal alkyl and an unsaturated hydrocarbon, which can be used to support a metal source, such as, for example, chromium, and a pyrrole-containing compound. The resultant catalyst systems can be used to oligomerize and/or trimerize olefins via a slurry process.

U.S. Pat. No. 5,523,507 discloses novel chromium-containing compounds prepared by forming a mixture of the chromium salt, a metal amide, and an ether either supported or unsupported. These novel chromium-containing compounds are activated by non-hydrolyzed alkyl aluminum compound and a Lewis acid.

U.S. Pat. No. 5,451,645 discloses novel chromium-containing compounds prepared by forming a mixture of a chromium salt, a metal amide, and an ether. These novel chromium-containing, or chromium pyrrolide compounds, with a metal alkyl and an unsaturated hydrocarbon, can be used as a co-catalyst system in the presence of an olefin polymerization catalyst system to produce a comonomer in-situ with trimerization.

U.S. Pat. No. 5,543,375 discloses a process to stabilize and/or reactivate an olefin production catalyst system, which comprises contacting an olefin production catalyst system, either before or after use, with an aromatic compound.

European Publication No. 0 668 106 discloses a process which will effectively deactivate, inhibit, and/or "kill" an olefin production catalyst, and halt polymer production in an olefin production process. It further provides for a process which can remove an olefin production catalyst from the product stream, and recover catalyst by-products for recycle, and/or recovery.

International Publication No. WO 99/19280 A1 discloses a process in which olefins are trimerized in the presence of a catalyst system comprising a chromium source, a pyrrole containing compound and a metal alkyl. The process is performed in a reactor and provides for a separator for collection of the desired products.

International Publication Nos. WO 2004/056478 and WO 2004/056479, disclose processes and catalysts to prepare an olefinic stream with more than 30% of 1-octene. The catalysts for this system are those that contain chromium or a chromium salt and a heteroatomic ligand.

Several pyridylamine catalyst complexes have been disclosed for the polymerization or copolymerization of ethylene, propylene, isobutylene, octene, and styrene by Symyx Technologies, Inc. in U.S. Pat. Nos. 6,713,577, 6,750,345, 6,706,829, 6,727,361, and 6,828,397. Pyridylamines were also disclosed in U.S. Pat. Nos. 6,103,657 and 6,320,005, assigned to Union Carbide Chemical and Plastics Technology Corporation, in which zirconium was used as the metal center, and the catalyst complex was used to polymerize alpha-olefins, and in U.S. Pat. No. 5,637,660, assigned to Lyondell Petrochemical Company, which also describes Group 4 complexes of pyridylamine ligands. Robertson et al., *Inorg. Chem.* 42, pp 6875-6885 (2003), discloses chromium complexes of tris(2-pyridylmethyl)amine for ethylene polymerization.

A need exists for improved processes to more effectively generate alpha-olefin comonomers. More particularly, a need exists for controlling and/or mitigating polymeric fouling in olefin oligomerization reactions. Such fouling reduction would provide benefits including but not limited to reducing/minimizing process down time, more efficiently and/or cost effectively producing desired olefin oligomers, reducing oligomerization reaction byproducts, and/or to reducing/minimizing inefficiencies associated with start-ups and shut-downs, among other reasons.

SUMMARY OF THE INVENTION

One aspect of the invention relates to a method for oligomerizing olefins comprising: contacting, in an oligomerization reactor under oligomerization conditions, a feed comprising an alpha-olefin, a catalyst having an olefin selectivity of at least 90 mol % to a desired oligomerization product, and optionally a diluent; producing an effluent comprising the desired oligomerization product, unreacted olefin, and polymer byproduct having at least 50 mol % of its repeat units based on the alpha-olefin and which causes fouling on one or more surfaces within the oligomerization reactor; and adding a polymer anti-foulant to the oligomerization reactor in an amount sufficient (i) to limit fouling on the one or more surfaces within the oligomerization reactor to no more than 20 grams of polymer byproduct per kilogram of desired oligomerization product (e.g., no more than 10 g/kg), (ii) to remediate, per kilogram of desired oligomerization product, at least 3 grams of polymer byproduct that has fouled on the one or more surfaces within the oligomerization reactor (e.g., at least 5 g/kg), or (iii) both (i) and (ii).

Another aspect of the invention relates to a method for reducing and/or inhibiting polymer fouling in an olefin oligomerization process, the method comprising selectively oligomerizing an alpha-olefin by contacting in an oligomerization reactor a feed comprising the alpha-olefin, a polymer anti-foulant, optionally a diluent, and a catalyst having an olefin selectivity of at least 90 mol % to a desired oligomerization product under reaction conditions sufficient to produce an effluent comprising the desired oligomerization product, unreacted olefin, and reaction byproducts comprising at least a (co)polymer, which has at least 50 mol % of its repeat units based on the alpha-olefin, and which causes fouling in the oligomerization reactor in the absence of the polymer anti-foulant, wherein the selective oligomerization containing the polymer anti-foulant reduces and/or inhibits fouling in the oligomerization reactor by at least 10% over a selective oligomerization with substantially no added polymer anti-foulant.

Yet another aspect of the invention relates to a method for polymerizing a polyethylene copolymer comprising contacting ethylene and an olefin oligomer product made according to the method of any of the prior aspects of the invention in a polymerization reactor under conditions sufficient to form a polyethylene copolymer.

DETAILED DESCRIPTION OF THE PREFERRED EMBODIMENTS

For the purposes of this invention and the claims thereto, when an oligomeric material (such as a dimer, trimer, tetramer, and/or pentamer) is referred to as comprising an olefin, the olefin present in the material is the reacted form of the olefin. Likewise, the active species in a catalytic cycle may comprise the neutral or ionic forms of the catalyst. In addition, a reactor is any container(s) in which a chemical reaction occurs.

As used herein, the "new" numbering scheme for the Periodic Table Groups is used as set out in CHEMICAL AND ENGINEERING NEWS, 63(5), 27 (1985).

As used herein, the term "about," whether in reference to a single value or a range of values, is defined according to the scope of the value(s) given the significant figures expressed. For instance, "about 99%" means from 98.50% to 99.49%; "about 99.0%" means from 98.950% to 99.049%; and "about 99.00% means from 98.9950% to 99.0049%.

For purposes of this invention, a catalyst system is defined to be the combination of an activator and a metal ligand complex or the combination of an activator, a ligand, and a metal precursor. A metal ligand complex is defined to be the product of the combination of a metal precursor and a ligand.

The phrase "optionally substituted" means that a moiety (such as a hydrocarbyl) may or may not be substituted. The term "substituted" means that at least one hydrogen atom bound to a carbon atom is replaced with a heteroatom containing group or a hydrocarbyl group. Further, when the term "substituted" or "optionally substituted" introduces a list of possible substituted groups, it is intended that the term apply to every member of that group. That is, the phrase "substituted alkyl, alkenyl, and alkynyl" is to be interpreted as "substituted alkyl, substituted alkenyl, and substituted alkynyl." Similarly, "optionally substituted alkyl, alkenyl, and alkynyl" is to be interpreted as "optionally substituted alkyl, optionally substituted alkenyl, and optionally substituted alkynyl."

The term "hydrocarbyl" as used herein refers to hydrocarbyl radicals containing 1 to 50 carbon atoms. Preferred hydrocarbyls contain 1 to 24 carbon atoms, more specifically 1 to 16 carbon atoms, including branched or unbranched, cyclic or acyclic, saturated or unsaturated species, such as alkyl groups, alkenyl groups, aryl groups, and the like. The term "olefin selectivity," as used herein with reference to a metal-ligand complex, to a catalyst system, and/or to a reaction process, refers to the percentage (herein mole percentage, unless otherwise specified) content of one or more specific olefins (olefin comonomers) in relation to the total olefin content of the non-polymeric reaction product (i.e., excluding any olefin reactants, excluding any olefin solvents and/or diluents, and excluding any polymeric product, as defined below, having a double bond, but including any oligomeric olefin product, as defined below). Similarly, the term "olefinic purity," as used herein with reference to a composition such as a desired olefin product, refers to the percentage (herein mole percentage, unless otherwise specified) content of the desired olefin product in relation to the total olefin content of the non-polymeric reaction product (i.e., excluding any olefin reactants, excluding any olefin solvents and/or diluents, and excluding any polymeric product, as defined below, having a double bond, but including any oligomeric olefin product, as defined below).

As used herein, the phrase "characterized by the formula" is not intended to be limiting and is used in the same way that "comprising" is commonly used. The term "independently selected" is used herein to indicate that the groups in question—e.g., $R_1$, $R_2$, $R_3$, $R_4$, and $R_5$—can be identical or different (e.g., $R_1$, $R_2$, $R_3$, $R_4$, and $R_5$ may all be substituted alkyls, or $R_1$ and $R_2$ may be a substituted alkyl and $R_3$ may be an aryl, etc.). Use of the singular includes use of the plural and vice versa (e.g., a hexane solvent, includes hexanes). A named R group will generally have the structure that is recognized in the art as corresponding to R groups having that name. For the purposes of illustration, representative certain groups are defined herein. These definitions are intended to supplement and illustrate, not preclude, the definitions known to those of skill in the art.

The term "saturated" refers to the lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like, and specifically includes alkenyl and alkynyl groups, as well as groups in which double bonds are delocalized, as in aryl and heteroaryl groups as defined below.

The terms "cyclo" and "cyclic" are used herein to refer to saturated or unsaturated radicals containing a single ring or multiple condensed rings. Suitable cyclic moieties include, for example, cyclopentyl, cyclohexyl, cyclooctenyl, bicyclooctyl, phenyl, napthyl, pyrrolyl, furyl, thiophenyl, imidazolyl, and the like. In particular embodiments, cyclic moieties include between 3 and 200 atoms other than hydrogen, between 3 and 50 atoms other than hydrogen or between 3 and 20 atoms other than hydrogen.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, sec-butyl, t-butyl, octyl, decyl, and the like, as well as cycloalkyl groups such as cyclopentyl, cyclohexyl and the like. Generally, although again not necessarily, alkyl groups herein may contain 1 to about 20 carbon atoms.

The term "aromatic" is used in its usual sense, including unsaturation that is essentially delocalized across several bonds around a ring. The term "aryl" as used herein refers to a group containing an aromatic ring. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, or phenanthrenyl. In particular embodiments, aryl substituents include 1 to about 200 atoms other than hydrogen, typically 1 to about 50 atoms other than hydrogen, and specifically 1 to about 20 atoms other than hydrogen. In some embodiments herein, multi-ring moieties are substituents and in such embodiments the multi-ring moiety can be attached at an appropriate atom. For example, "naphthyl" can include 1-naphthyl or 2-naphthyl; "anthracenyl" can include 1-anthracenyl, 2-anthracenyl or 9-anthracenyl; and "phenanthrenyl" can include 1-phenanthrenyl, 2-phenanthrenyl, 3-phenanthrenyl, 4-phenanthrenyl, or 9-phenanthrenyl.

The term "alkoxy" as used herein intends an alkyl group bound through a single, terminal ether linkage; that is, an "alkoxy" group may be represented as —O-alkyl where alkyl is as defined above. The term "aryloxy" is used in a similar fashion, and may be represented as —O-aryl, with aryl as defined below. The term "hydroxy" refers to —OH.

The terms "halo" and "halogen" are used in the conventional sense to refer to a chloro, bromo, fluoro or iodo radical.

The terms "heterocycle" and "heterocyclic" refer to a cyclic radical, including ring-fused systems, including heteroaryl groups as defined below, in which one or more carbon atoms in a ring is replaced with a heteroatom—that is, an atom other than carbon, such as nitrogen, oxygen, sulfur, phosphorus, boron or silicon. Heterocycles and heterocyclic groups include saturated and unsaturated moieties, including heteroaryl groups as defined below. Specific examples of heterocycles include pyridine, pyrrolidine, pyrroline, furan, tetrahydrofuran, thiophene, imidazole, oxazole, thiazole, indole, and the like, including any isomers of these. Additional heterocycles are described, for example, in Alan R. Katritzky, *Handbook of Heterocyclic Chemistry*, Pergammon Press, 1985, and in *Comprehensive Heterocyclic Chemistry*, A. R. Katritzky et al., eds., Elsevier, 2d. ed., 1996.

The term "heteroaryl" refers to an aryl radical that includes one or more heteroatoms in the aromatic ring. Specific heteroaryl groups include groups containing heteroaromatic rings such as thiophene, pyridine, pyrazine, isoxazole, pyrazole, pyrrole, furan, thiazole, oxazole, imidazole, isothiazole, oxadiazole, triazole, and benzo-fused analogues of these rings, such as indole, carbazole, benzofuran, benzothiophene, and the like.

More generally, the modifiers "hetero" and "heteroatom-containing", as in "heteroalkyl" or "heteroatom-containing hydrocarbyl group" refer to a molecule or molecular fragment in which one or more carbon atoms is replaced with a heteroatom. Thus, for example, the term "heteroalkyl" refers to an alkyl substituent that is heteroatom-containing. The term "heteroatom-containing" is considered an adjectival term herein and is thus treated similarly to the term "substituted."

Throughout the instant specification, the presence of one solid line and one dashed line between any pair of atoms is intended to indicate that the bond in question may be a single bond or a double bond, or a bond with bond order intermediate between single and double, such as the delocalized bonding in an aromatic ring. Furthermore, the presence of an arrow with a dotted line between any pair of atoms is intended to indicate that the bond in question is not a covalent bond but is an associative bond, e.g., such as a dative bond, wherein there is some interaction (e.g., hydrogen-bonding, bonding involving partial atomic charges, pi-bonding, lone pair-transition metal d-orbital bonding, lone-pair-Lanthanide/Actinide f-orbital bonding, or the like, or some combination thereof) between the pair of atoms stronger than van der Waals interactions.

Throughout the instant specification, several abbreviations may be used to refer to specific compounds or elements. Abbreviations for atoms are as given in the periodic table (Li=lithium, for example). Other abbreviations that may be used are as follows: "i-Pr" to refer to isopropyl; "t-Bu" to refer to tertiary-butyl; "i-Bu" to refer to isobutyl; "Me" to refer to methyl; "Et" to refer to ethyl; "Ph" to refer to phenyl; "Mes" to refer to mesityl (2,4,6-trimethyl phenyl); "TFA" to refer to trifluoroacetate; "THF" to refer to tetrahydrofuran; "TsOH" to refer to para-toluenesulfonic acid; "cat." to refer to catalytic amount of; "LDA" to refer to lithium diisopropylamide; "DMF" to refer to dimethylformamide; "eq." to refer to molar equivalents; "TMA" to refer to $AlMe_3$; "TIBA" to refer to $Al\text{-}(Bu)_3$; and the like.

As used herein, the term "poly[olefin] (co)polymer" should be understood to include homopolymers and copolymers wherein at least about 80% by weight, preferably at least about 85% by weight, more preferably at least about 90% by weight, for example at least about 95% by weight, at least about 98% by weight, at least about 99% by weight, at least about 99.5% by weight, at least about 99.9% by weight, or about 100% by weight, as synthesized, of the monomer repeat units are based on a repeat unit structure of a specific alpha-olefin. For example, where the [olefin] is ethylene, the repeat unit structure would be —$(CH_2—CH_2)$—. In embodiments where one or more co-monomers are included in polyethylene polymer(s), as synthesized, the one or more co-monomers can be collectively present in an amount of not more than about 20% by weight, preferably not more than about 15% by weight, more preferably not more than about 10% by weight, for example not more than about 5% by weight, not more than about 2% by weight, not more than about 1% by weight, not more than about 0.5% by weight, or not more than about 0.1% by weight. The one or more co-monomers, when present, can preferably include, but are not limited to, $C_3$-$C_{10}$ alpha-olefins (e.g., propylene, 1-butene, 1-hexene, 1-octene, and 1-decene), more preferably $C_4$-$C_8$ alpha-olefins such as 1-butene, 1-hexene, and/or 1-octene. In a preferred embodiment, the one or more co-monomers, when present, can be substantially free from dienes and polyunsaturated compounds.

As used herein, the phrase "substantially no added," in reference to a component in a composition, should be understood to mean that no more than about 0.1% by weight, preferably no more than about 0.05% by weight, for example no more than about 0.02% by weight, no more than about 0.01% by weight, no more than about 0.0005% by weight, or absolutely none, of the component, based on the entire weight of the composition, is added to the composition.

As referred to herein, selective oligomerization refers to producing the desired oligomer(s) with a selectivity of the reaction being at least 80%, more specifically at least 90%, by mole of desired oligomer(s), with the possibility that an acceptable amount of polymer is present, but with the preference that no polymer is present in the product. In other embodiments, less than 10 wt % of polymer is formed by the selective oligomerization reaction, specifically less than 5 wt %, more specifically less than 2 wt %, based upon the total weight of monomer converted to oligomers and polymers, where a polymer is defined to mean a molecule comprising more than 50 mers (repeat units). An "oligomer" as used herein is defined to mean a molecule comprising from 2 to 50 mers (repeat units); however, desired oligomers are defined as described herein, but preferably do not contain more than 20 total carbons and/or preferably do not contain more than 10 repeat units. In other embodiments, selective oligomerization refers to producing one or two desired oligomers, with the selectivity of the one or two desired oligomers summing to at least 80%, e.g., at least 90%, by sum of total moles of oligomers. Particularly preferred desired oligomers are molecules consisting of 3 to 10 mers with an olefinic unsaturation at the end of the oligomer (i.e., alpha-olefin oligomers).

As referred to herein, the terms "fouling polymer" and "fouled polymer" are synonymous and refer to polymer that not only has become insoluble in the oligomerization reaction medium under oligomerization conditions but also has deposited on one or more surfaces within the oligomerization reactor, which includes not only the walls of the reactor but also on surfaces of other implements inside the reactor (e.g., impellers, baffles, and the like), such that the fouling/fouled polymer remains within the reactor (i.e., does not exit the reactor during the ordinary course of the reaction).

The invention relates primarily to olefin oligomerization methods and methods for reducing/inhibiting fouling in olefin oligomerizations comprising: contacting, in an oligomerization reactor (e.g., under oligomerization conditions), an alpha-olefin feed, a catalyst having an olefin selectivity of at least 90 mol % or at least 92 mol % or at least 94 mol % to a desired oligomerization product, a polymer anti-foulant, and optionally a diluent; selectively producing an effluent comprising the desired oligomerization product, unreacted olefin, and alpha-olefin-based polymer byproduct that causes fouling. The amount of polymer anti-foulant can be chosen to limit fouling to no more than 20 grams (e.g., no more than 10 grams) polymer byproduct per kilogram of desired oligomerization product, to remediate at least 3 grams (e.g., at least 5 grams) fouled polymer per kilogram of desired oligomerization product, and/or to reduce and/or inhibit polymer fouling by at least 10% (e.g., at least 20%) over a selective oligomerization with substantially no added polymer anti-foulant.

Any of the methods according to the invention can further comprise the step of separating the desired oligomerization product from the effluent to attain an olefinic purity of desired oligomerization product of at least 90 mol %, for example at least 93 mol %, at least 95 mol %, at least 96 mol %, at least 97 mol %, or at least 98 mol % in the separated effluent.

While the feed comprising the alpha-olefin (the alpha-olefin feed) can contain one or more $C_2$-$C_{12}$ alpha-olefins, the most preferred alpha-olefin for the oligomerization reactions described herein is ethylene. As a result, in a preferred embodiment, the alpha-olefin feed comprises greater than about 99 wt % ethylene.

In one embodiment, the oligomerization conditions can include a reaction temperature from about 60° C. to about 150° C., a reaction pressure from about 300 psi (2.1 MPa) to about 900 psi (6.2 MPa), and optionally but preferably a reaction residence time from about 30 minutes to about 4 hours.

A particularly useful catalyst system that can be utilized for selective oligomerization processes can be formed from the combination of:
1) a ligand characterized by the following general formula:

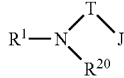

wherein:
$R^1$ and $R^{20}$ are each independently selected from the group consisting of consisting of hydrogen and optionally substituted hydrocarbyl, heteroatom containing hydrocarbyl and silyl (alternately $R^1$ and $R^{20}$ are each independently selected from the group consisting of: hydrogen and optionally substituted alkyl, heteroalkyl, cycloalkyl, heterocycloalkyl, aryl, heteroaryl, silyl and combinations thereof), provided that $R^1$ or $R^{20}$ do not equal T-J (alternately $R^1$ and $R^{20}$ are each independently a ring having from 4 to 8 atoms in the ring selected from the group consisting of substituted cycloalkyl, heterocycloalkyl, aryl and heteroaryl);

T is a bridging group, preferably represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms (for example, T is cyclopropyl, where T'=C, and $R^2$ and $R^3$ together form —$CH_2$—$CH_2$—; or T is cyclohexyl, where T'=C and the two $R^2$ groups together form —$CH_2$—$CH_2$—$CH_2$—$CH_2$—); and J is an optionally substituted six-membered heterocycle, containing at least one nitrogen atom as part of the ring, or J is an optionally substituted five-membered heterocycle, containing at least one nitrogen atom as part of the ring;

2) a metal precursor compound characterized by the general formula Cr(L)$_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; and n is 1, 2, 3, 4, 5, or 6; and 3) optionally, one or more activators.

In one embodiment, the ligand, as shown above, can be characterized by the following general formula, where J is a pyridyl or substituted pyridyl group:

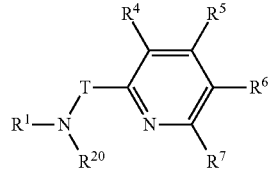

where $R^1$, $R^{20}$ and T are as described above; and $R^4$, $R^5$, $R^6$ and $R^7$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$, $R^6$ and $R^7$ groups may be joined to form one or more optionally substituted ring systems.

In another embodiment, the ligand can be characterized by the following general formula:

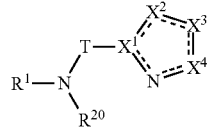

where $R^1$, $R^{20}$, and T are as described above; and $X^1$ is nitrogen or —C($R^8$)$_{n'}$—, $X^2$, $X^3$, and $X^4$ are selected from the group consisting of oxygen, sulfur, —C($R^8$)$_{n'}$—, —N-($R^8$)$_{n''}$—, and provided that at least one of $X^1$, $X^2$, $X^3$, or $X^4$ is carbon or —C($R^8$)$_{n'}$—; each n' can be 1 or 2 and each n" can be 0 or 1; and, each $R^8$ can be independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, and $R^8$ groups may be joined to form one or more optionally substituted ring systems.

In one embodiment, $R^1$ and $R^{20}$ are each independently selected from the group consisting of hydrogen and optionally substituted alkyl, heteroalkyl, aryl, heteroaryl, silyl and combinations thereof. In another embodiment, $R^1$ and $R^{20}$ are each independently a ring having from 4 to 8 atoms in the ring generally selected from the group consisting of substituted cycloalkyl, heterocycloalkyl, aryl, and heteroaryl.

In another embodiment (including all those described above), $R^{20}$ is hydrogen and $R^1$ is selected from the group consisting of alkyl, substituted alkyl, aryl, and substituted aryl.

In still another embodiment (including all those described above), $R^1$ and $R^{20}$ can each be independently selected from hydrogen and optionally substituted alkyl groups.

In yet another embodiment (including all those described above), $R^1$ and $R^{20}$ are joined in a ring structure having from 3 to 50 non-hydrogen atoms. In one variation of the immediately prior embodiment, the ring structure formed by the joining of $R^1$ and $R^{20}$ preferably does not include an optionally substituted heteroaryl ring having from 5 to 8 ring carbons, and more preferably does not include an optionally substituted pyrrolyl ring.

In another embodiment (including all those described above), $R^1$ is not hydrogen when $R^{20}$ is a cyclic group.

In still another embodiment (including all those described above), $R^{20}$ is not a hydrogen when $R^1$ is a cyclic group.

In another embodiment (including all those described above), $R^7$ is selected from the group consisting of optionally substituted aryl and heteroaryl.

In another embodiment (including all those described above), $R^2$ is hydrogen, and $R^3$ is selected from the group consisting of aryl, substituted aryl, heteroaryl, substituted heteroaryl, alkyl, and substituted alkyl groups, and —$PY_2$ where Y is selected from the group consisting of aryl, substituted aryl, heteroaryl, and substituted heteroaryl.

In some embodiments (including all those described above), $R^1$ is hydrogen and $R^{20}$ is selected from the group consisting of methyl, ethyl, propyl, butyl, pentyl, hexyl, octyl, decyl, docecyl, benzyl, and —$CH_2CH_2Ph$ groups.

In some embodiments (including all those described above), $R^1$ and $R^{20}$ are each independently selected from the group consisting of methyl, ethyl, propyl, butyl, pentyl, hexyl, octyl, decyl, docecyl, benzyl, and —$CH_2CH_2Ph$ groups.

In some embodiments (including all those described above), $R^5$ is selected from the group consisting of —$CF_3$, —H, —F, —Cl, —$N(Me)_2$ and —OR, wherein R is an optionally substituted alkyl group, an optionally substituted benzyl group, or an optionally substituted aryl group.

In some embodiments (including all those described above), $R^3$ is selected from the group consisting of hydrogen and optionally substituted alkyl, heteroalkyl, cycloalkyl, heterocycloalkyl, silyl, and combinations thereof.

The heterocycle-amine ligands, such as pyridylamine ligands, described herein can be prepared according to the procedures known to those of ordinary skill in the art, for example, as described in U.S. Pat. Nos. 6,750,345, 6,713,577, 7,414,006, and 7,425,661, the disclosures of all of which are incorporated by reference herein.

Preferred ligands for use herein include pyridylamine ligands in general, as well as specifically those represented by the following formulae:

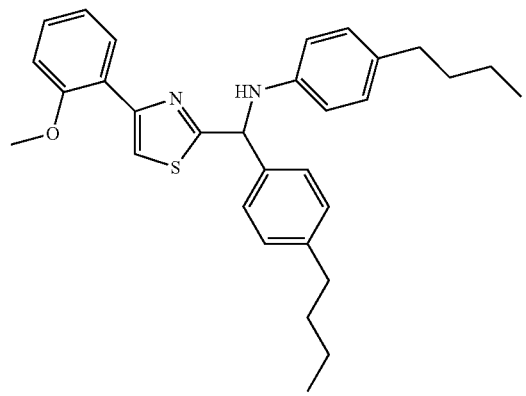

B1

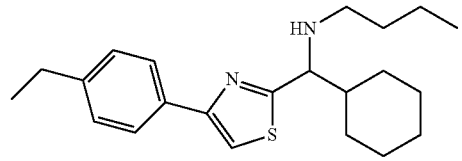

B2

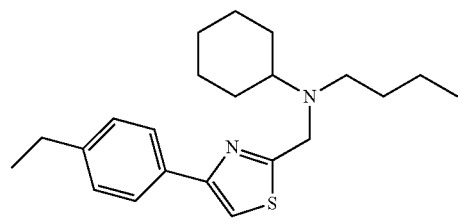

B3

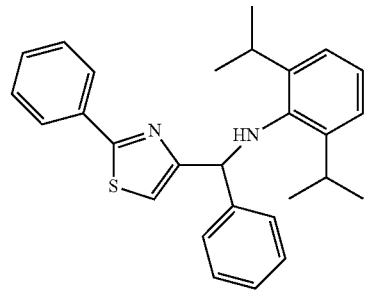

C1

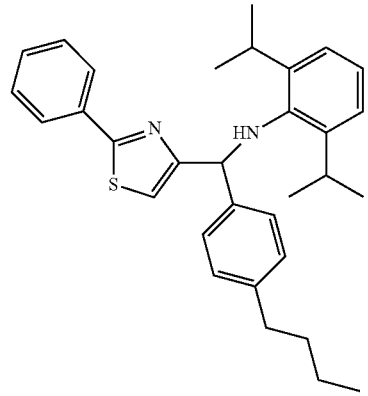

C2

-continued
C3
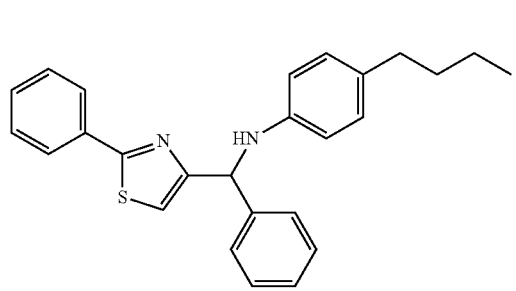
C4
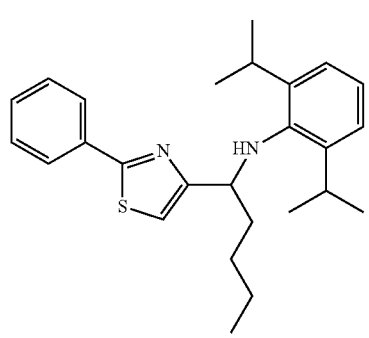
C5
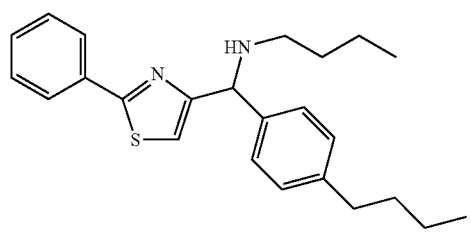
D1
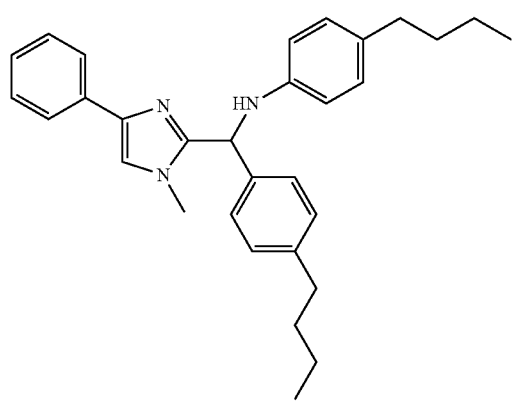
-continued
D2
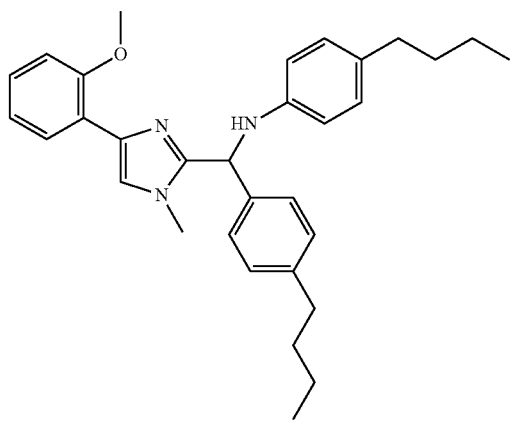
D3
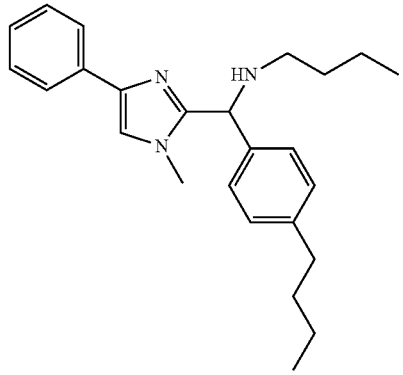
D4
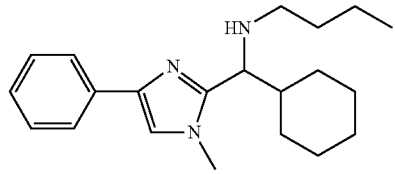
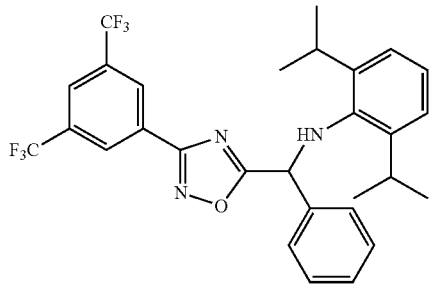
E1

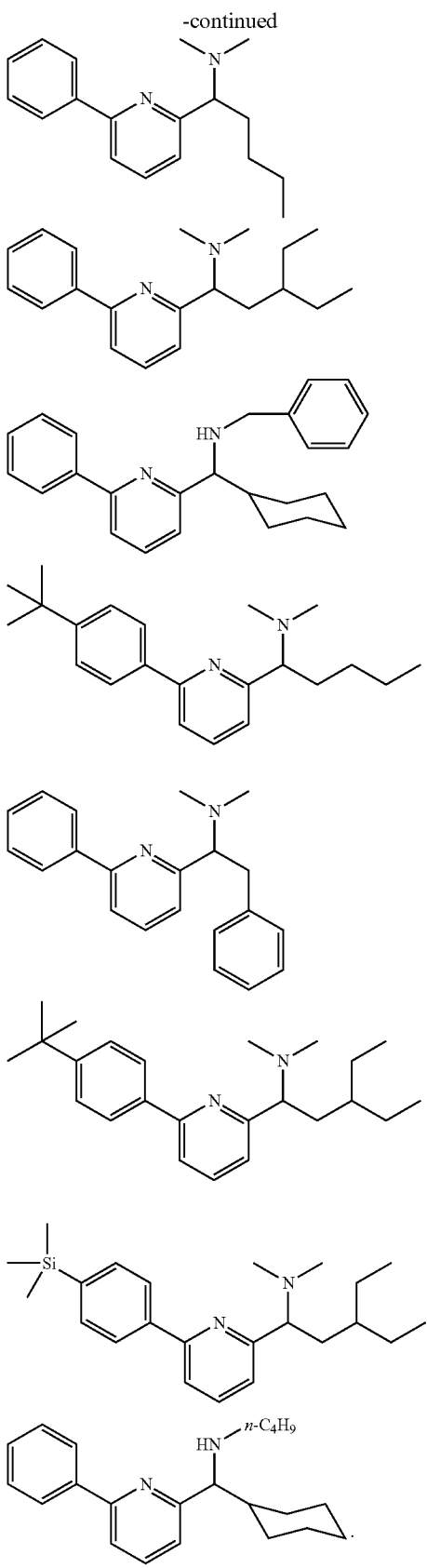

Particularly useful ethylene trimerization ligands useful herein include:

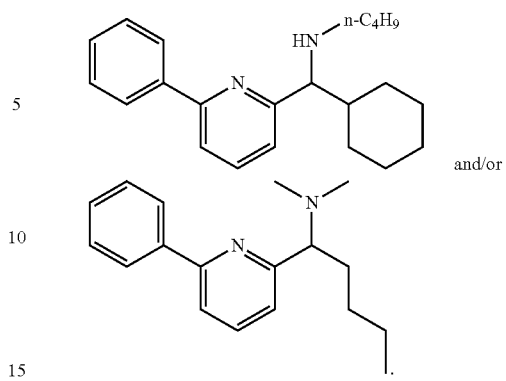

and/or

Pyridylamine ligands can be synthesized by any reasonable methods, e.g., those described in U.S. Pat. No. 7,425,661 and/or U.S. patent application Ser. No. 12/192,843, filed Aug. 15, 2008.

Once the desired ligand is formed, it can be combined with a Cr atom, ion, compound, or other Cr precursor compound, and, in some embodiments, the present invention encompasses compositions that include any of the above-mentioned ligands, in combination with an appropriate Cr precursor and an optional activator.

Particularly useful Cr metal precursor compounds are represented by the formula $Cr(L)_n$, where L is an organic group, an inorganic group, or an anionic atom, and where n is an integer of 1 to 6, and, when n is not less than 2, each L may be the same or different from each other. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof. Optionally, two or more L groups can be joined into a ring structure. One or more of the ligands L may be ionically bonded to Cr and, for example, L may be a non-coordinated, loosely-coordinated, or weakly-coordinated anion (e.g., L may be selected from the group consisting of those anions described below in the conjunction with the activators). See Marks et al., Chem. Rev. 100, pp 1391-1434 (2000) for a detailed discussion of these weak interactions. The chromium precursors may be monomeric, dimeric, or higher orders thereof.

In a preferred embodiment, each L is independently a hydrocarbyl, halide, alkoxy, carboxylate, diaonate, amino, ether, or amine. In an alternate embodiment, each L is independently chloride, mesityl, tetrahydrofuran, methyl, ethyl, butyl, pentyl, hexyl, octyl, phenyl, $Et_2O$, $NH_3$, $NMe_3$, acetylacetonate, 2-ethylhexanoate, neopentyl, $SMe_2$, $CH_2$—$C_6H_4$—O—$NMe_2$, trifluoroacetate, $CH(SiMe_3)_2$, p-tolyl, diisopropylamide, picolinate, or $NO_3$,= where Et is ethyl and Me is methyl.

Specific examples of suitable chromium precursors include, but are not limited to, $(THF)_3CrMeCl_2$, $(Mes)_3Cr(THF)$, $[\{TFA\}_2Cr(OEt_2)]_2$, $(THF)_3CrPh_3$, $CrCl_3(THF)_3$, $CrCl_4(NH_3)_2$, $Cr(NMe_3)_2Cl_3$, $CrCl_3$, $Cr(acac)_3$, $Cr(2$-ethylhexanoate$)_3$, $Cr(neopentyl)_4$, $Cr(CH_2$—$C_6H_4$-o-$NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p$-tolyl$)Cl_2(THF)_3$, $Cr(diisopropylamide)_3$, $Cr(picolinate)_3$, $[Cr_2Me_8][Li(THF)]_4$, $CrCl_2(THF)$, $Cr(NO_3)_3$, $[CrMe_6][Li(Et_2O)]_3$, $[CrPh_6][Li(THF)]_3$, $[CrPh_6][Li(n$-$Bu_2O)]_3$, $[Cr(C_4H_8)_3][Li(THF)]_3$, and other well known chromium compounds commonly used as precursors in the formation of Cr complexes and catalysts.

Preferred metal precursors used herein can be selected from the group consisting of (THF)$_3$CrMeCl$_2$, (THF)$_3$CrCl$_3$, (Mes)$_3$Cr(THF), [{TFA}$_2$Cr(OEt$_2$)]$_2$, (THF)$_3$CrPh$_3$, and mixtures thereof.

The ligand may be mixed with a metal precursor compound prior to, or simultaneously with, allowing the mixture to be contacted with the reactants (e.g., monomers). The ligand to metal precursor compound ratio can be in the range of about 0.01:1 to about 100:1, more specifically in the range of about 0.1:1 to about 10:1.

Cr-ligand complexes can take a number of different coordination modes. General examples of possible coordination modes include those characterized by the following general formulas:

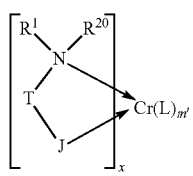
VI (a)

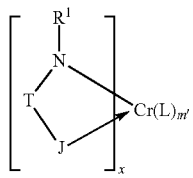
VI (b)

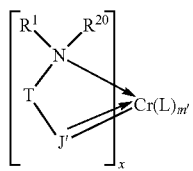
VI (c)

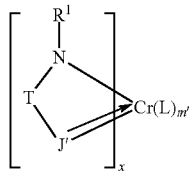
VI (d)

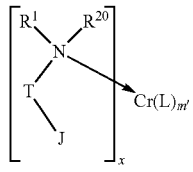
VI (e)

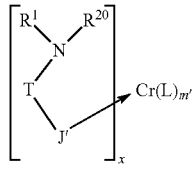
VI (f)

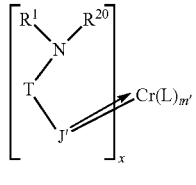
VI (g)

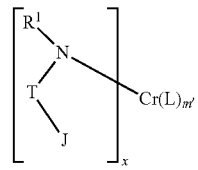
VI (h)

wherein R$^1$, R$^{20}$, L, J, and T are described above; wherein x is 1 or 2; and wherein m' is 1, 2, 3, 4, or 5. J' is defined the same as J is defined above, provided that J' includes 2 atoms bonded to the Cr, one of which is in the ring position adjacent to the atom bonded to T, which is bonded to Cr through a dative bond, and the other of which is bonded to the Cr through a covalent bond. Numerous other coordination modes are possible, for example the ligands may bind to two chromium metal centers in a bridging fashion (see, for example, Cotton and Walton, *Multiple Bonds Between Metal Atoms* 1993, Oxford University Press).

In some embodiments, the ligand may be mixed with a suitable metal precursor prior to, or simultaneous with, allowing the mixture to be contacted to the reactants. When the ligand is mixed with the metal precursor, a metal-ligand complex can be formed. In connection with the metal-ligand complex and depending on the ligand(s) chosen, the metal-ligand complex may take the form of dimers, trimers, or higher orders thereof, or there may be two or more metal atoms that are bridged by one or more ligands. Furthermore, two or more ligands may coordinate with a single metal atom. The exact nature of the metal-ligand complex(es) formed can depend on the chemistry of the ligand and on the method of combining the metal precursor and ligand, such that a distribution of metal-ligand complexes may form, with the number of ligands bound to the metal being greater than, equal to, or less than the number of equivalents of ligands added relative to an equivalent of metal precursor.

In one embodiment, metal ligand complexes (such as the Cr-ligand complex described above) can advantageously coordinate such that the metal (e.g., Cr) is associated with (e.g., covalently and/or datively bonded to) the nitrogen atom (N), one or more atoms of the J or J' moiety, or both. Additionally or alternately, when R$^1$ and R$^{20}$ are joined in a ring structure having from 3 to 50 non-hydrogen atoms, the metal (e.g., Cr) of the metal ligand complex (e.g., the Cr-ligand complex) is preferably not associated with (e.g., covalently and/or datively bonded to) any atom(s) other than the nitrogen atom (N) on the ring formed by N, R$^1$, and R$^{20}$.

In one embodiment, the metal complex is represented by the formula:

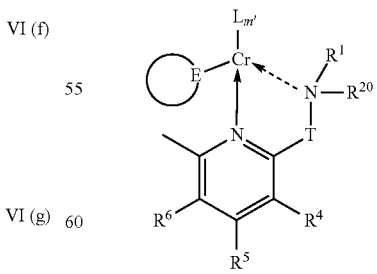

wherein R$^1$, R$^4$, R$^5$, R$^6$, R$^{20}$, T, L, and m' are as described above; and E is a carbon atom that is part of an optionally substituted aryl or heteroaryl ring. In one aspect, the aryl or heteroaryl ring may be polycyclic.

Listed below are some non-limiting examples of Cr-Ligand complex embodiments useful herein:

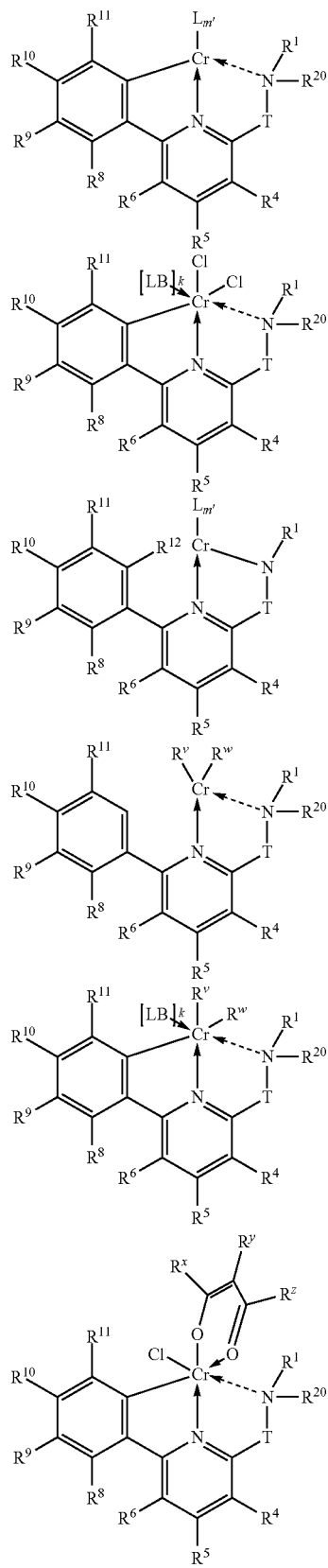

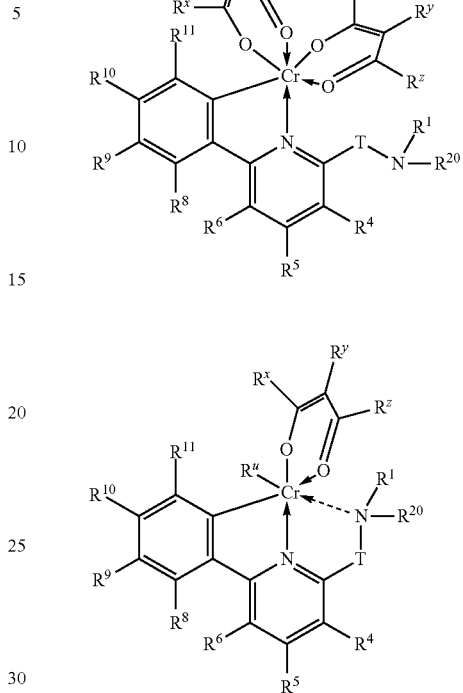

wherein
R$^1$, R$^2$, R$^3$, R$^4$, R$^5$, R$^6$, R$^{20}$, T, L, and m' are as defined above;

R$^8$ R$^9$, R$^{10}$, R$^{11}$, and R$^{12}$ are independently selected from the group consisting of hydrogen, halogen, nitro, optionally substituted alkyl, heteroalkyl, aryl, heteroaryl, alkoxy, aryloxy, silyl, boryl, phosphino, amino, alkylthio, and arylthio, and combinations thereof; and optionally two or more R$^8$, R$^9$, R$^{10}$, R$^{11}$, and R$^{12}$ groups may be joined to form one or more optionally substituted ring systems;

R$^u$, R$^v$, R$^w$, R$^x$, R$^y$, and R$^z$ are optionally substituted alkyl, heteroalkyl, aryl, and/or heteroaryl moieties;

a dashed arrow indicates that the dative bond is an optional bond, which may or may not be present; and LB is a Lewis base; and k=0 or 1.

Some specific embodiments of Cr-Ligand complexes useful herein are shown below:

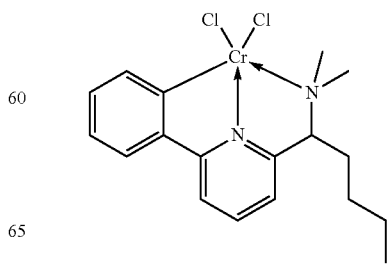

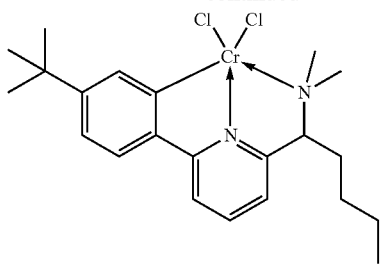
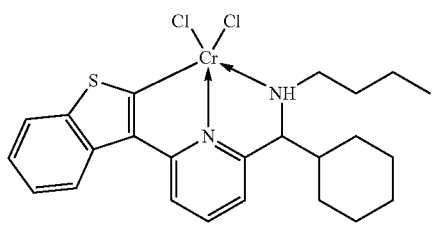
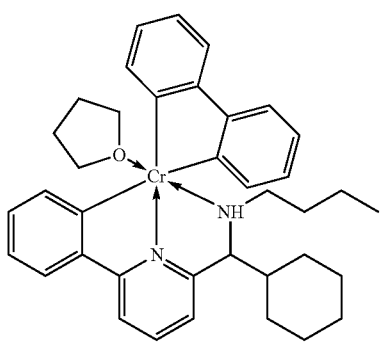
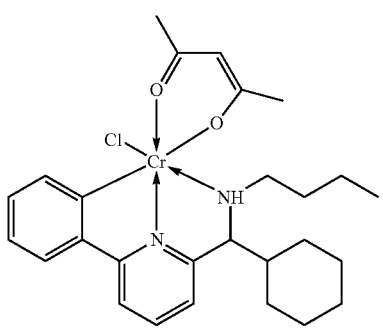
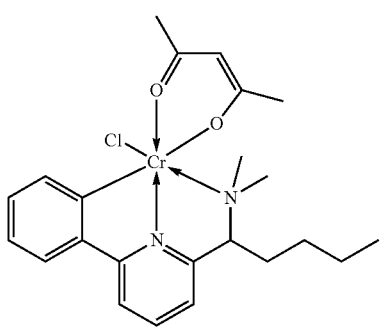
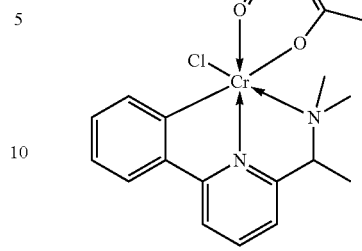
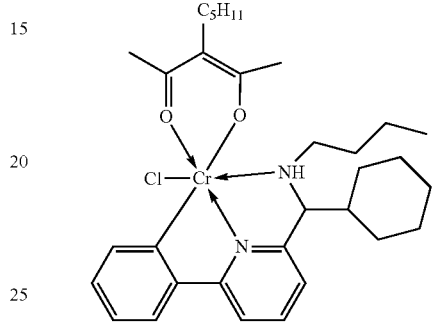
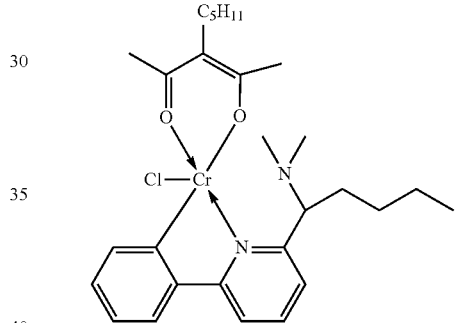
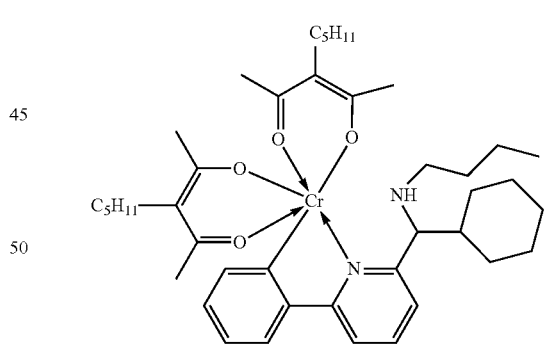
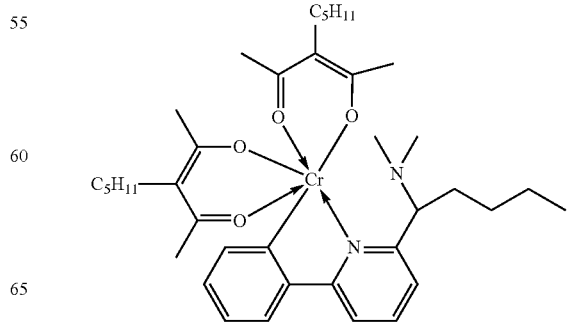

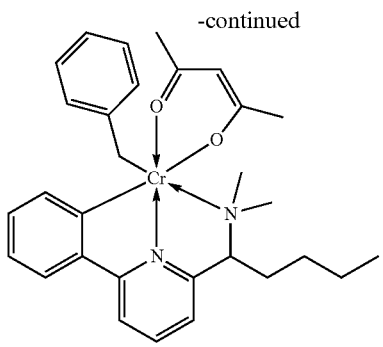

Further description of such complexes and how to prepare them is disclosed in U.S. Patent Application Ser. No. 60/841,226, filed Aug. 30, 2006, assigned to ExxonMobil Chemical Patents Inc., the entire contents of which are hereby incorporated by reference.

The ligand-metal-precursor combinations and the metal ligand complexes, described above, are optionally activated in various ways to yield compositions active for selective oligomerization (preferably ethylene oligomerization). For the purposes of this patent specification and appended claims, the terms "cocatalyst" and "activator" are used herein interchangeably and are defined to be any compound which can activate any one of the ligands-metal-precursor-combinations and the metal ligand complexes described above by converting the combination, complex, or composition into a catalytically active species. Non-limiting activators, for example, include alumoxanes, aluminum alkyls, other metal or main group alkyl or aryl compounds, ionizing activators, which may be neutral or ionic, Lewis acids, reducing agents, oxidizing agents, and combinations thereof.

In one embodiment, alumoxane activators are utilized as an activator in the compositions useful in the invention. Alumoxanes are generally oligomeric compounds containing —Al(R*)—O— sub-units, where R* is an alkyl group. Examples of alumoxanes include methylalumoxane (MAO), ethylalumoxane, isobutylalumoxane, and modified methylalumoxanes (MMAO), which include alkyl groups other than methyl such as ethyl, isobutyl, and n-octyl, such as MMAO-3A, PMAO-IP (referring to polymethylalumoxane, improved process, manufactured by Akzo-Nobel and meaning an MAO prepared from a non-hydrolytic process). Alkylalumoxanes and modified alkylalumoxanes are suitable as catalyst activators, particularly when the abstractable ligand of the catalyst is a halide, alkoxide, or amide. Mixtures of different alumoxanes and modified alumoxanes may also be used. For further descriptions on production and use of alumoxanes, see U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, and 5,329,032; see also European Publication Nos. EP 0 561 476 A1, EP 0 279 586 B1, EP 0 516 476 A1, and EP 0 594 218 A1; see also International Publication No. WO 94/10180.

When the activator is an alumoxane (modified or unmodified), some embodiments select the maximum amount of activator at a 5000-fold molar excess Al/Cr over the catalyst precursor. The minimum preferred activator-to-catalyst-precursor is a 1:1 molar ratio. More specifically, the Al/Cr ratio can be from 1000:1 to 100:1.

It may be preferable to use a visually clear methylalumoxane. A cloudy or gelled alumoxane can be filtered to produce a clear solution, or clear alumoxane can be decanted from the cloudy solution. Another particularly useful alumoxane is a modified methyl alumoxane (MMAO) cocatalyst type 3A (commercially available from Akzo Chemicals, Inc., under the trade name Modified Methylalumoxane type 3A, and disclosed in U.S. Pat. No. 5,041,584).

Aluminum alkyl or organoaluminum compounds which may be utilized as activators (or scavengers) include, but are not limited to, trimethylaluminum, triethylaluminum, tri-isobutylaluminum, tri-n-hexylaluminum, tri-n-octylaluminum, diisobutylaluminum hydride, ethylaluminum dichloride, diethylaluminum chloride, diethylaluminum ethoxide, and the like.

In some embodiments, the activator includes compounds that may abstract a ligand making the metal complex cationic and providing a charge-balancing non-coordinating or weakly-coordinating anion. The term "non-coordinating anion" (NCA) means an anion which either does not coordinate to said cation or which is only weakly coordinated to said cation, thereby remaining sufficiently labile to be displaced by a neutral Lewis base.

It is within the scope of this invention to use an ionizing or stoichiometric activator, neutral or ionic, such as tri-(n-butyl)-ammonium tetrakis(pentafluorophenyl)boron, a tris(perfluorophenyl)boron metalloid precursor, or a tris(perfluoronaphthyl)boron metalloid precursor, polyhalogenated heteroborane anions (International Publication No. WO 98/43983), boric acid (U.S. Pat. No. 5,942,459), or a combination thereof. It is also within the scope of this invention to use neutral or ionic activators alone or in combination with alumoxane or modified alumoxane activators.

Examples of neutral stoichiometric activators include, but are not limited to, tri-substituted boron, tellurium, aluminum, gallium, and indium, or mixtures thereof. The three substituent groups of the tri-substituted metal can each be independently selected from alkyls, alkenyls, halogens, substituted alkyls, aryls, arylhalides, alkoxyls, and halides. In some embodiments, the three substituent groups can be independently selected from halogen, mono or multicyclic (including halosubstituted) aryls, alkyls, and alkenyl compounds, and mixtures thereof; preferred include alkenyl groups having 1 to 20 carbon atoms, alkyl groups having 1 to 20 carbon atoms, alkoxy groups having 1 to 20 carbon atoms, and aryl groups having 3 to 20 carbon atoms (including heteroaryls and substituted aryls). In other embodiments, one or more of the three substituent groups can be alkyls having 1 to 4 carbon groups, phenyls, naphthyls, or mixtures thereof. In further embodiments, one or more of the three substituent groups can be halogenated, specifically fluorinated, aryl groups. In even further embodiments, the neutral stoichiometric activator can be tris(perfluorophenyl)boron or tris(perfluoronaphthyl)boron.

Ionic stoichiometric activator compounds may contain an active proton, or some other cation associated with, but not coordinated to, or only loosely coordinated to, the remaining ion of the ionizing compound. Such compounds and the like are described in European Publication Nos. EP 0 277 003 A1, EP 0 277 004 A1, EP 0 495 375 A1, EP 0 500 944 B1, EP 0 520 732 A1, and EP 0 570 982 A1; in U.S. Pat. Nos. 5,066,741, 5,153,157, 5,198,401, 5,206,197, 5,241,025, 5,384,299, and 5,502,124; and in U.S. patent application Ser. No. 08/285,380, filed Aug. 3, 1994, the entire disclosure of each of which is herein fully incorporated by reference.

Ionic catalysts can be prepared by reacting a metal (e.g., Cr) compound with some neutral Lewis acids, such as $B(C_6F_6)_3$, which, upon reaction with the abstractable ligand (X) of the metal (e.g., Cr) compound, can form an anion, such as $([B(C_6F_5)_3(X)]^-)$, which can stabilize the cationic metal (e.g., Cr) species generated by the reaction. The catalysts can be prepared with activator components which are ionic compounds or compositions.

In some embodiments, compounds useful as an activator component in the preparation of the ionic catalyst systems used in the process of this invention can comprise a cation, which is optionally a Brönsted acid capable of donating a proton, and a compatible non-coordinating anion, which is capable of stabilizing the active catalyst species, and which can be formed when the two compounds are combined, and said anion will typically be sufficiently labile to be displaced by olefinic substrates or other neutral Lewis bases, such as ethers, nitriles, and the like. Two classes of compatible non-coordinating anions useful herein have been disclosed in European Publication Nos. EP 0 277 003 A1 and EP 0 277 004 A1, both published in 1988 (anionic coordination complexes comprising a plurality of lipophilic radicals covalently coordinated to and shielding a central charge-bearing metal or metalloid core, and anions comprising a plurality of boron atoms such as carboranes, metallacarboranes, and boranes).

Illustrative, but not limiting, examples of boron compounds that may be used as an activating cocatalyst herein include tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)-ammonium tetraphenylborate, N,N-dimethylanilinium tetraphenylborate, N,N-diethyl-anilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate, triethylsilylium tetraphenylborate, benzene(diazonium)tetraphenylborate, trimethylammonium tetrakis(pentafluorophenyl)borate, triethylammonium tetrakis-(pentafluorophenyl)borate, tripropylammonium tetrakis (pentafluorophenyl)borate, tri(n-butyl)ammonium tetrakis (pentafluorophenyl)borate, tri(sec-butyl)ammonium tetrakis-(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenyl-carbenium tetrakis(pentafluorophenyl)borate, triphenylphosphonium tetrakis(penta-fluorophenyl)borate, triethylsilylium tetrakis (pentafluorophenyl)borate, benzene-(diazonium)tetrakis (pentafluorophenyl)borate, strimethylammonium tetrakis-(2,3,4,6-tetrafluorophenyl)-borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetra-fluorophenyl)-borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis (perfluoronaphthyl)borate, triethylammonium tetrakis (perfluoronaphthyl)$_b$ orate, tripropylammonium tetrakis (perfluoronaphthyl)borate, tri(n-butyl)ammonium tetrakis-(perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis-(perfluoronaphthyl)borate, N,N-dimethyl-(2,4,6-trimethylanilinium)tetrakis-(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis-(perfluoronaphthyl)borate, trimethylammonium tetrakis(perfluorobiphenyl)borate, triethylammonium tetrakis(perfluorobiphenyl)borate, tripropylammonium tetrakis-(perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis-(perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, tropillium tetrakis-(perfluorobiphenyl)borate, triphenylcarbenium tetrakis(perfluorobiphenyl)borate, triphenyl-phosphonium tetrakis(perfluorobiphenyl)borate, triethylsilylium tetrakis(perfluorobiphenyl)-borate, benzene(diazonium)tetrakis(perfluorobiphenyl)borate, trimethylammonium tetrakis (3,5-bis(trifluoromethylphenyl)borate, triethylammonium tetrakis(3,5-bis(trifluoro-methylphenyl)borate, tripropylammonium tetrakis(3,5-bis(trifluoromethylphenyl)borate, tri(n-butyl)ammonium tetrakis(3,5-bis(trifluoromethylphenyl)borate, tri(t-butyl)ammonium tetrakis(3,5-bis (trifluoromethylphenyl)borate, N,N-dimethylanilinium tetrakis(3,5-bis(trifluoromethylphenyl)borate, N,N-diethylanilinium tetrakis(3,5-bis(trifluoro-methylphenyl)borate, N,N-dimethyl-(2,4,6-trimethylanilinium)tetrakis(3,5-bis(trifluoro-methylphenyl)borate, tropillium tetrakis(3,5-bis(trifluoromethylphenyl)borate, triphenyl-carbenium tetrakis(3,5-bis(trifluoromethylphenyl)borate, triphenylphosphonium tetrakis(3,5-bis(trifluoromethylphenyl)borate, triethylsilylium tetrakis(3,5-bis(trifluoromethylphenyl)-borate, benzene (diazonium)tetrakis(3,5-bis(trifluoromethylphenyl)borate, dialkyl ammonium salts such as di-(i-propyl)ammonium tetrakis(pentafluorophenyl)borate and dicyclohexyl-ammonium tetrakis(pentafluorophenyl)borate, additional tri-substituted phosphonium salts such as tri(o-tolyl)phosphonium tetrakis(pentafluorophenyl)borate and tri(2,6-dimethyl-phenyl)phosphonium tetrakis(pentafluorophenyl)borate, and mixtures thereof.

Specifically useful ionic stoichiometric activators can include, but are not limited to N,N-dimethylanilinium tetra (perfluorophenyl)borate, N,N-dimethylanilinium tetrakis (perfluoronaphthyl)borate, N,N-dimethylanilinium tetrakis (perfluorobiphenyl)borate, N,N-dimethylanilinium tetrakis (3,5-bis(trifluoromethylphenyl)borate, triphenylcarbenium tetrakis(perfluoronaphthyl)borate, triphenylcarbenium tetrakis(perfluorobiphenyl)borate, triphenylcarbenium tetrakis (3,5-bis(trifluoromethylphenyl)borate, triphenylcarbenium tetrakis(perfluorophenyl)borate, and mixtures thereof.

Other examples of preferred ionizing activators can include, but are not limited to, $HNMe(C_{18}H_{37})_2^+B(C_6F_5)_4^-$, $HNPh(C_{18}H_{37})_2^+B(C_6F_5)_4^-$, $((4-n-Bu-C_6H_4)NH(n-hexyl)_2)^+B(C_6F_5)_4^-$, and $((4-n-Bu-C_6H_4)NH(n-decyl)_2)^+B(C_6F_5)_4^-$. Specific preferred $(L^*-H)^+$ cations include N,N-dialkylanilinium cations such as $HNMe_2Ph^+$, substituted N,N-dialkylanilinium cations such as $(4-n-Bu-C_6H_4)NH(n-C_6H_{13})_2^+$ and $(4-n-Bu-C_6H_4)NH(n-C_{10}H_{21})_2^+$, and $HNMe(C_{18}H_{37})_2^+$. Specific examples of anions include tetrakis(3,5-bis(trifluoromethylphenyl)borate and tetrakis (pentafluorophenyl)borate.

In one embodiment, activation methods using ionizing ionic compounds not containing an active proton but capable of producing an active oligomerization catalyst are also contemplated. Such methods are described in relation to metallocene catalyst compounds, e.g., as disclosed in European Publication Nos. EP 0 426 637 A1 and EP 0 573 403 A1, as well as in U.S. Pat. No. 5,387,568, the disclosures of all of which are incorporated herein by reference.

The process can also employ cocatalyst compounds or activator compounds that are initially neutral Lewis acids but form a cationic metal complex and a noncoordinating anion, or a zwitterionic complex, upon reaction with the compounds of this invention. For example, tris(pentafluorophenyl) boron or aluminum may act to abstract a hydrocarbyl or hydride ligand to yield a cationic metal complex and stabilizing non-coordinating anion.

In some embodiments, ionizing activators may be employed as described in Köhn et al. (*J. Organomet. Chem.*, 683, pp 200-208, (2003)) to, for example, improve solubility.

In another embodiment, the aforementioned cocatalyst compounds can also react with the compounds to produce a neutral, uncharged catalyst capable of selective ethylene oligomerization. For example, Lewis acidic reagents such as, for example, alkyl or aryl aluminum or boron compounds, can abstract a Lewis basic ligand such as, for example, THF or $Et_2O$, from a compound yielding a coordinatively unsaturated catalyst capable of selective ethylene oligomerization.

When the cations of noncoordinating anion precursors are Brönsted acids such as protons or protonated Lewis bases (excluding water), or reducible Lewis acids such as ferrocenium or silver cations, or alkali or alkaline earth metal cations such as those of sodium, magnesium, or lithium, the activator-to-catalyst-precursor molar ratio may be any ratio; however, useful ratios can include, but are not limited to, those from 1000:1 to 1:1.

Combinations of two or more activators may also be used in the practice of this invention.

Another suitable ion forming, activating cocatalyst comprises a salt of a cationic oxidizing agent and a noncoordinating, compatible anion characterized by the general formula:

$$(OX^{e+})_d(A^{d-})_e$$

where $OX^{e+}$ is a cationic oxidizing agent having a charge of e+; e is an integer from 1 to 3; d is an integer from 1 to 3, and $A^{d-}$ is as previously defined. Examples of cationic oxidizing agents include, but are not limited to, ferrocenium, hydrocarbyl-substituted ferrocenium, $Ag^+$, $Pb^{+2}$, and combinations thereof. Preferred embodiments of $A^{d-}$ are those anions previously defined with respect to the Brönsted acid containing activators, especially tetrakis-(pentafluorophenyl)borate.

Other general activators or compounds useful in an oligomerization reaction may be used. These compounds may be activators in some contexts, but may also serve other functions in the reaction system, such as alkylating a metal center or scavenging impurities. These compounds are within the general definition of "activator," but are not considered herein to be ion-forming activators. These compounds can include a group 13 reagent that may be characterized by the formula $G^{13}R^{50}{}_{3-p}D_p$, where $G^{13}$ is selected from the group consisting of B, Al, Ga, In, and combinations thereof, where p is 0, 1, or 2, each $R^{50}$ is independently selected from the group consisting of hydrogen, halogen, optionally substituted alkyl, alkenyl, alkynyl, heteroalkyl, heteroalkenyl, heteroalkynyl, aryl, or heteroaryl, and combinations thereof, and where each D is independently selected from the group consisting of halogen, hydrogen, alkoxy, aryloxy, amino, mercapto, alkylthio, arylthio, phosphino, and combinations thereof.

In other embodiments, a divalent metal reagent may be used that is characterized by the general formula $M'R^{50}{}_{2-p'}D_{p'}$, where p' can be 0 or 1 and where $R^{50}$ and D are as defined above. M' is the metal and can be selected from the group consisting of Mg, Ca, Sr, Ba, Zn, Cd, Cu, and combinations thereof.

In still other embodiments, an alkali metal reagent may be used that is defined by the general formula $M^{iv}R^{50}$, where $R^{50}$ is as defined above, and where $M^{iv}$ is the alkali metal and can be selected from the group consisting of Li, Na, K, Rb, Cs, and combinations thereof. Additionally, hydrogen and/or silanes may be used in the catalytic composition and/or added to the polymerization system. Silanes may be characterized by the formula $SiR^{50}{}_{4-q}D_q$, where $R^{50}$ and D are defined as above, with the proviso that at least one D is hydrogen in this embodiment, and where q is 1, 2, 3, or 4.

Non-limiting examples of Group 13 reagents, divalent metal reagents, and alkali metal reagents useful as activators for the catalyst compounds described above can include: methyl lithium, butyl lithium, phenyl lithium, dihexylmercury, butylmagnesium, diethylcadmium, benzylpotassium, diethyl zinc, tri-n-butyl aluminum, diisobutyl ethylboron, diethylcadmium, di-n-butyl zinc, tri-n-amyl boron, in particular the aluminum alkyls such as trihexyl-aluminum, triethylaluminum, trimethylaluminum, and triisobutyl aluminum, diisobutyl aluminum bromide, diethylaluminum chloride, ethylaluminum dichloride, isobutyl boron dichloride, methyl magnesium chloride, ethyl beryllium chloride, ethyl calcium bromide, diisobutyl aluminum hydride, methyl cadmium hydride, diethyl boron hydride, hexylberyllium hydride, dipropylboron hydride, octylmagnesium hydride, butyl zinc hydride, dichloroboron hydride, di-bromo-aluminum hydride, and bromocadmium hydride. Additionally or alternately, other Group 13 reagents, divalent metal reagents, and alkali metal reagents useful as activators for the catalyst compounds described above are known to those in the art, and a more complete discussion of these compounds may be found, e.g., in U.S. Pat. Nos. 3,221,002 and 5,093,415, both of which are herein fully incorporated by reference.

Other activators include those described in International Publication No. WO 98/07515, incorporated herein by reference, such as tris(2,2',2"-nonafluorobiphenyl)fluoroaluminate, which publication is fully incorporated herein by reference. Combinations of activators also contemplated by the invention can include, for example, alumoxanes and ionizing activators in combinations; see, for example, European Publication No. EP 0 573 120 B1, International Publication Nos. WO 94/07928 and WO 95/14044, and U.S. Pat. Nos. 5,153,157 and 5,453,410, the disclosures of all of which are herein fully incorporated by reference.

Other suitable activators are disclosed in International Publication No. WO 98/09996, incorporated herein by reference, which describes activating bulky ligand metallocene catalyst compounds with perchlorates, periodates, and iodates, including their hydrates. International Publication Nos. WO 98/30602 and WO 98/30603, incorporated herein by reference, describe the use of lithium (2,2'-bisphenyl-ditrimethylsilicate).4THF as an activator for a bulky ligand metallocene catalyst compound. International Publication No. WO 99/18135, incorporated herein by reference, describes the use of organoboron-aluminum activators. European Publication No. EP 0 781 299 B1 describes using a silylium salt in combination with a non-coordinating compatible anion. Also, methods of activation, such as using radiation (see European Publication No. EP 0 615 981 B1, incorporated herein by reference), electro-chemical oxidation, and the like, are also contemplated as activating methods for the purposes of rendering the chromium complexes or compositions active for the selective oligomerization of olefins. Other activators or methods are described, for example, in U.S. Pat. Nos.

5,849,852, 5,859,653, and 5,869,723, and in International Publication Nos. WO 98/32775 and WO 99/42467 (dioctadecylmethylammonium-bis(tris(pentafluorophenyl)borane) benzimidazolide), all of which are incorporated herein by reference.

Additional optional activators include metal salts of non-coordinating or weakly-coordinating anions, for example where the metal can be selected from Li, Na, K, Ag, Ti, Zn, Mg, Cs, and Ba.

It is within the scope of this invention that metal-ligand complexes and/or ligand-metal-precursor-combinations can be combined with one or more activators or activation methods described above. For example, a combination of activators has been described in U.S. Pat. Nos. 5,153,157 and 5,453,410, in European Publication No. EP 0 573 120 B1, and in International Publication Nos. WO 94/07928 and WO 95/14044. These documents all discuss the use of an alumoxane in combination with an ionizing activator.

Preferred activators used in the method of the present invention can be selected from the group consisting of modified methylalumoxane (MMAO), methylalumoxane (MAO), trimethylaluminum (TMA), triisobutyl aluminum (TIBA), polymethylalumoxane-IP (PMAO), N,N-di(n-decyl)-4-n-butyl-anilinium tetrakis-(perfluorophenyl)borate, and mixtures thereof.

Typically, the molar ratio of metal (from the metal-ligand complex or the ligand-metal-precursor combination) to activator (specifically Cr:activator, or alternately Cr:Al or Cr:B) can range from 1:1 to 1:5000. In another embodiment, the molar ratio of metal to activator employed can range from 1:1 to 1:500. In another embodiment, the molar ratio of metal to activator employed can range from 1:1 to 1:50. In another embodiment, the molar ratio of chromium to activator employed can range from 1:1 to 1:500. In another embodiment, the molar ratio of chromium to activator employed can range from 1:1 to 1:50.

In embodiments where more than one activator is used, the order in which the activators are combined with the metal-ligand complex or the ligand-metal-precursor combination may be varied.

Very generally, the oligomerization can be carried out in the Ziegler-Natta or Kaminsky-Sinn methodology, including temperatures from −100° C. to 300° C. and pressures from atmospheric to 3000 atmospheres (303.9 MPa). Suspension, solution, slurry, gas phase, or high-pressure oligomerization processes may be employed with the processes of this invention. Such processes can be run in a batch, semi-batch, or continuous mode.

Suitable solvents and/or diluents for oligomerization are non-coordinating, inert liquids. Examples include, but are not limited to, mineral oil; straight and branched-chain hydrocarbons, such as propane, isobutane, butane, pentane, isopentane, hexane, isohexane, heptane, octane, dodecane, and mixtures thereof; cyclic and alicyclic hydrocarbons, such as cyclohexane, cycloheptane, methylcyclohexane, methylcycloheptane, and mixtures thereof; perhalogenated hydrocarbons such as perfluorinated $C_{4-10}$ alkanes; chlorobenzenes; and aromatic and alkylsubstituted aromatic compounds, such as benzene, toluene, mesitylene, and xylene. Suitable solvents and/or diluents may additionally or alternately include liquid olefins, which may act as monomers or comonomers, including, but not limited to, ethylene, propylene, 1-butene, 1-hexene, 1-pentene, 3-methyl-1-pentene, 4-methyl-1-pentene, 1-octene, 1-decene, and mixtures thereof. With regard to catalyst solvent and/or diluent, there is flexibility as far as what catalyst solvent and/or diluent may be used. Particularly preferred solvents and/or diluents can include, but are not limited to, the comonomer product (e.g., 1-butene, 1-hexene, 1-octene, 1-decene, combinations thereof, etc.), propane, $C_{4+}$ paraffins (e.g., isopentane, isobutane, butane, pentane, etc.), cycloparaffins, and aromatics (e.g., toluene). In one embodiment, where diluent is present, the diluent can be advantageously selected from the group consisting of 1-butene, 1-hexene, 1-octene, toluene, propane, butane, isobutane, pentane, isopentane, and combinations thereof. In a preferred embodiment, when the diluent is present, the diluent can be selected from the group consisting of one or more $C_3$-$C_8$ linear, branched, and/or cyclic hydrocarbons.

If the catalyst is in the form of an immobilized or fixed bed, it may not require additional solvent and/or diluent. In another exemplary embodiment, the catalyst to the comonomer synthesis reactor may be provided in the form of an immobilized or fixed bed, hence reducing and/or eliminating the need for a solvent and/or diluent altogether.

Other additives that are useful in an oligomerization reaction may be employed, such as scavengers, promoters, modifiers, reducing agents, oxidizing agents, dihydrogen, aluminum alkyls, and/or silanes. For example, Jolly et al. (*Organometallics*, 16, pp 1511-1513 (1997)) has reported the use of magnesium as a reducing agent for Cr compounds that were synthesized as models for intermediates in selective ethylene oligomerization reactions.

In some useful embodiments, the activator (such as methylalumoxane or modified methylalumoxane-3A) can be combined with the metal-ligand-complex or the ligand-metal-precursor-combination immediately prior to introduction into the reactor. Such mixing may be achieved by mixing in a separate tank, followed by swift injection into the reactor, by mixing in-line just prior to injection into the reactor, or the like. It has been observed that in some instances, a short activation time can be very useful. Likewise, in situ activation, where the catalyst system components are injected separately into the reactor, with or without monomer, and allowed to combine within the reactor directly, can also be useful in the practice of this invention. In some embodiments, the catalyst system components are allowed to contact each other for 30 minutes or less, prior to contact with monomer, alternately for 5 minutes or less, alternately for 3 minutes or less, alternately for 1 minute or less.

The oligomer synthesis reactor may take various forms, including but not limited to, a stirred tank, a (longer, thinner) tube-like contactor, or a bubble column. In an alternative embodiment, two or more oligomer synthesis reactors can be configured in series. An advantage of series reactors can be more thorough utilization of the catalyst, i.e., less nearly-fresh catalyst will get discharged with the product. Heat exchange capacity can also be incorporated in the reactor or in a pumparound loop, to limit the exotherm. For instance, heat exchange can be incorporated into the reactor by cooling and condensing vapors generated by the reaction and by returning the condensed liquid to the reactor, e.g., as reflux; this heat exchange in the reactor can advantageously make cooling surfaces in the reactor less susceptible to fouling, e.g., by polymer, catalyst residue, oligomers, etc. Where waxy buildup is an issue, spare heat exchangers may also be provided. Depending on the operating pressure of the reactor, the amount of the ethylene dissolved in the catalyst solvent and/or diluent may also be controlled, which can add flexibility in the design of the reactor and the process as a whole.

Oligomer synthesis reaction conditions of the instant invention can be selected and controlled to yield from about 20% to about 99%, for example from about 40% to about 95% or from about 60% to about 90%, single pass conversion of feed olefin (e.g., ethylene). In some embodiments, particularly where a relatively low single pass conversion of feed olefin (e.g., ethylene) is desired, the oligomer synthesis reaction conditions can be selected and controlled to yield a single pass conversion of feed olefin (e.g., ethylene) from about 10% to about 60%, for example from about 10% to about 50%, from about 10% to about 40%, from about 20% to about 50%, from about 20% to about 40%, from about 30% to about 50%, from about 25% to about 55%, from about 35% to about 55%, from about 35% to about 45%, from about 25% to about 45%, from about 20% to about 35%, from about 10% to about 30%, from about 15% to about 45%, or from about 15% to about 55%. In other embodiments, particularly where a relatively medium single pass conversion of feed olefin (e.g., ethylene) is desired, the oligomer synthesis reaction conditions can be selected and controlled to yield a single pass conversion of feed olefin (e.g., ethylene) from about 30% to about 80%, for example from about 40% to about 70%, from about 30% to about 60%, from about 30% to about 50%, from about 30% to about 70%, from about 40% to about 60%, from about 35% to about 75%, from about 35% to about 65%, from about 35% to about 55%, from about 45% to about 75%, from about 45% to about 65%, from about 50% to about 80%, from about 40% to about 70%, or from about 50% to about 75%.

For some of the chromium catalysts disclosed in U.S. Pat. No. 5,543,375, a range of reaction conditions are disclosed, which are herein incorporated by reference. One exemplary, but non-limiting, set of reactor conditions includes a temperature from about 60-150° C. or from about 80-150° C., and a pressure from about 300-900 psi (~21.1-63.3 kg/cm$^2$) or from about 300-700 psi (~21.1-49.2 kg/cm$^2$). A preferred range of reactor temperatures with ethylene can be from about 60-110° C. Reaction conditions may be tuned to obtain desired phase separations, as well as reactivity. In addition, reactor residence time is flexible, and may be chosen to provide a desired level of ethylene conversion. The residence time is typically a function of the type and amount of the catalyst utilized. In one exemplary embodiment, when utilizing the chromium type catalysts disclosed in U.S. Pat. No. 5,543,375, the average residence time can range from about 30 minutes to about 4 hours for a backmixed or pumparound reactor where most of the catalyst in the reactor at a given time is not "fresh," but has been circulating around for some time, and has become partially deactivated.

In an exemplary embodiment where a very active and very selective catalyst is utilized to produce 1-hexene, a light catalyst solvent and/or diluent may be used such that 1-hexene is collected as the bottom of the distillation column in very high purity, while the catalyst solvent and/or diluent and the ethylene from the overhead are recycled back to the oligomer synthesis reactor.

The desired oligomerization product (olefin comonomer(s)) produced via the aforementioned processes may be homopolymerized, used as a comonomer input of a polyolefin (co)polymerization process, and/or utilized in a variety of other applications.

In one preferred embodiment, the desired oligomerization product can be selected from the group consisting of 1-butene, 1-hexene, 1-octene, 1-decene, and mixtures thereof. In another preferred embodiment, the desired oligomerization product can comprise 1-hexene, 1-octene, or a combination thereof.

In another preferred embodiment, the catalyst has an olefin selectivity of at least 95 mol %, for example at least 97 mol % or at least 98 mol % to the desired oligomerization product. Additionally or alternately, the catalyst can have an olefin selectivity of at least 95 mol % to the desired oligomerization product, which can advantageously be two olefins selected from the group consisting of 1-butene, 1-hexene, 1-octene, and 1-decene.

In another embodiment, the polymer anti-foulant particles can have a density from 0.921 g/cm$^3$ to about 0.980 g/cm$^3$, preferably from about 0.935 g/cm$^3$ to about 0.980 g/cm$^3$, for example from 0.941 g/cm$^3$ to about 0.975 g/cm$^3$. Additionally or alternately, it may be desirable for the polymer anti-foulant particle density to be no less than 0.921 g/cm$^3$, for example no less than 0.930 g/cm$^3$, no less than 0.935 g/cm$^3$, or no less than 0.941 g/cm$^3$.

In a particularly preferred embodiment, the polymer anti-foulant can comprise, or can be, a high-density polyethylene polymer (HDPE). In another preferred embodiment, the polymer anti-foulant can comprise a polyethylene homopolymer or a polyethylene copolymer having less than about 6 wt % comonomer repeat units (e.g., less than about 5 wt % comonomer repeat units, less than about 3 wt % comonomer repeat units, less than about 2 wt % comonomer repeat units, or less than about 1 wt % comonomer repeat units). Advantageously, in one embodiment, the polymer anti-foulant can have a chemical composition similar to the polymer byproduct that is fouling or has fouled the oligomerization reactor (e.g., in the previous embodiment, the polymer byproduct can also comprise a polyethylene homopolymer or a polyethylene copolymer having less than about 6 wt % comonomer repeat units).

In another embodiment, the polymer anti-foulant particles can have a particle size distribution such that its average particle size, $d_{50}$, can be at least about 100 microns, for example at least about 100 microns, at least about 150 microns, at least about 200 microns, at least about 250 microns, at least about 300 microns, at least about 350 microns, at least about 400 microns, at least about 450 microns, at least about 500 microns, at least about 550 microns, at least about 600 microns, at least about 700 microns, at least about 800 microns, at least about 900 microns, or at least about 1 mm. Additionally or alternately, the polymer anti-foulant particles can have a particle size distribution such that its $d_{90}$ (i.e., at least 90% of the particles have a particle size at or above the given value) is at least about 50 microns, for example at least about 75 microns, at least about 100 microns, at least about 150 microns, at least about 200 microns, at least about 250 microns, at least about 300 microns, at least about 350 microns, at least about 400 microns, at least about 450 microns, or at least about 500 microns.

In another preferred embodiment, at least one of the following is(are) satisfied: the polymer anti-foulant has a density of at least about 0.921 g/cm$^3$; the polymer anti-foulant has an average particle size, $d_{50}$, of at least about 100 microns; the polymer anti-foulant comprises a polyethylene homopolymer or a polyethylene copolymer having less than about 6 wt % comonomer repeat units; the amount of polymer anti-foulant is sufficient to limit fouling on the one or more surfaces within the oligomerization reactor to no more than 10 grams of polymer byproduct per kilogram of desired oligomerization product; the alpha-olefin comprises ethylene; the desired oligomerization product comprises 1-hexene, 1-octene, 1-decene, or a combination thereof; the polymer byproduct comprises a polyethylene (co)polymer; the diluent is selected from the group consisting of one or more $C_3$-$C_8$ linear, branched, and/or cyclic hydrocarbons; and the polymer anti-foulant reduces and/or inhibits fouling in the oligomerization reactor by at least 10% over a selective oligomerization with substantially no added polymer anti-foulant.

In another embodiment, the polymer anti-foulant is treated prior to addition to the oligomerization reactor to reduce water and oxygen content in the polymer anti-foulant to a level sufficient to prevent significant deactivation of the oligomerization catalyst. One such effective means of treating the polymer anti-foulant is to heat the polymer anti-foulant particles in a substantially inert atmosphere. Heating can be to a temperature greater than or equal to 60° C. or greater than or equal to 80° C. or greater than or equal to 100° C., but must not exceed the melting temperature of the polymer anti-foulant. Heating can be for a time greater than or equal to 15 minutes or greater than or equal to 30 minutes or greater than or equal to 60 minutes. The inert atmosphere may be produced by purging the space around the polymer anti-foulant particles with any inert gas, including but not limited to nitrogen.

Another aspect of the invention involves a method for polymerizing a polyolefin (e.g., polyethylene) copolymer comprising contacting a $C_2$-$C_{12}$ alpha-olefin (e.g., ethylene) and a desired olefin oligomer product (e.g., 1-hexene and/or 1-octene) made according to any of the methods previously described herein in a polymerization reactor under conditions sufficient to form a polyolefin (e.g., polyethylene) copolymer. The method for polymerizing a polyolefin copolymer can additionally or alternately comprise the steps of forming a desired olefin oligomer product, particularly one having reduced/inhibited fouling, according to any of the previously described methods, and then contacting that desired olefin oligomer product with the $C_2$-$C_{12}$ alpha-olefin in a polymerization reactor under conditions sufficient to form a polyolefin (e.g., polyethylene) copolymer. Additionally or alternately, though not preferably, the desired olefin oligomer product according to the invention can be homopolymerized under conditions sufficient to form a poly(olefin oligomer) homopolymer.

Additionally or alternately, the present invention can include the following embodiments.

Embodiment 1. A method for oligomerizing olefins comprising: contacting, in an oligomerization reactor under oligomerization conditions, a feed comprising an alpha-olefin, a catalyst having an olefin selectivity of at least 90 mol % to a desired oligomerization product, and optionally a diluent; producing an effluent comprising the desired oligomerization product, unreacted olefin, and polymer byproduct having at least 50 mol % of its repeat units based on the alpha-olefin and which causes fouling on one or more surfaces within the oligomerization reactor; and adding a polymer anti-foulant to the oligomerization reactor.

Embodiment 2. The method of embodiment 1 wherein the polymer anti-foulant is treated prior to addition to the oligomerization reactor to reduce water and oxygen content in the polymer anti-foulant to a level sufficient to prevent significant deactivation of the catalyst.

Embodiment 3. The method of embodiment 2 wherein the treatment comprises heating the polymer anti-foulant in a substantially inert atmosphere.

Embodiment 4. The method of embodiment 1 in which the polymer anti-foulant is added to the oligomerization reactor in an amount sufficient (i) to limit fouling on the one or more surfaces within the oligomerization reactor to no more than 20 grams of polymer byproduct per kilogram of desired oligomerization product, (ii) to remediate, per kilogram of desired oligomerization product, at least 3 grams of polymer byproduct that has fouled on the one or more surfaces within the oligomerization reactor, or (iii) both (i) and (ii).

Embodiment 5. A method for reducing and/or inhibiting polymeric fouling in an olefin oligomerization process, the method comprising: selectively oligomerizing an alpha-olefin by contacting in an oligomerization reactor a feed comprising the alpha-olefin, a polymer anti-foulant, optionally a diluent, and a catalyst having an olefin selectivity of at least 90 mol % to a desired oligomerization product under reaction conditions sufficient to produce an effluent comprising the desired oligomerization product, unreacted olefin, and reaction byproducts comprising at least a (co)polymer, which has at least 50 mol % of its repeat units based on the alpha-olefin, and which causes fouling in the oligomerization reactor in the absence of the polymer anti-foulant, wherein the selective oligomerization containing the polymer anti-foulant reduces and/or inhibits fouling in the oligomerization reactor by at least 10% over a selective oligomerization with substantially no added polymer anti-foulant.

Embodiment 6. The method of embodiment 1 or embodiment 2, further comprising the step of separating the desired oligomerization product from the effluent to attain an olefinic purity of desired oligomerization product of at least 98 mol %.

Embodiment 7. The method of any of the previous embodiments, wherein the catalyst comprises the combination of: a) a ligand represented by the formula:

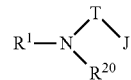

wherein: N is nitrogen; $R^1$ and $R^{20}$ are each independently selected from the group consisting of hydrogen, optionally substituted hydrocarbyl, heteroatom containing hydrocarbyl, and silyl, provided that $R^1$ or $R^{20}$ do not equal T-J, or alternately $R^1$ and $R^{20}$ are each independently a ring having from 4 to 8 atoms in the ring selected from the group consisting of substituted cycloalkyl, heterocycloalkyl, aryl, and heteroaryl; T is a bridging group, preferably represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms; and J is an optionally substituted six-membered heterocycle, containing at least one nitrogen atom as part of the ring, or J is an optionally substituted five-membered heterocycle, containing at least one nitrogen atom as part of the ring; b) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers, and combinations thereof, wherein two or more L groups may be combined in a ring structure having from 3 to 50 non-hydrogen atoms; and n is 1, 2, 3, 4, 5, or 6; and c) optionally, one or more activators.

Embodiment 8. The method of any of the previous embodiments, wherein the feed comprises greater than about 99 wt % ethylene.

Embodiment 9. The method of any of the previous embodiments, wherein the ligand of the catalyst is represented by at least one of the following formulas:

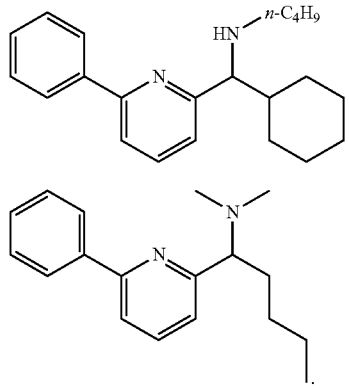

Embodiment 10. The method of any of the previous embodiments, wherein the diluent is present and is selected from the group consisting of 1-butene, 1-hexene, 1-octene, toluene, propane, butane, isobutane, pentane, isopentane, and combinations thereof.

Embodiment 11. The method of any of the previous embodiments, wherein the oligomerization conditions and/or the reaction conditions comprise a reaction temperature from about 60° C. to about 150° C., a reaction pressure from about 300 psi (21.1 kg/cm$^2$) to about 900 psi (63.3 kg/cm$^2$), and optionally a reaction residence time from about 30 minutes to about 4 hours.

Embodiment 12. The method of any of the previous embodiments, wherein the desired oligomerization product is selected from the group consisting of 1-butene, 1-hexene, 1-octene, 1-decene, and mixtures thereof.

Embodiment 13. The method of embodiment 10, wherein the catalyst has an olefin selectivity of at least 95 mol %, preferably at least 97 mol %, for instance at least 98.5 mol %, to the desired oligomerization product.

Embodiment 14. The method of embodiment 10 or embodiment 11, wherein the catalyst has an olefin selectivity of at least 95 mol % to the desired oligomerization product, which is two olefins selected from the group consisting of 1-butene, 1-hexene, 1-octene, and 1-decene.

Embodiment 15. The method of any of the previous embodiments, wherein one or more of the following are satisfied: the polymer anti-foulant has a density of at least about 0.921 g/cm$^3$; the polymer anti-foulant has an average particle size, $d_{50}$, of at least about 100 microns; the polymer anti-foulant comprises a polyethylene homopolymer or a polyethylene copolymer having less than about 6 wt % comonomer repeat units; the amount of polymer anti-foulant is sufficient to limit fouling on the one or more surfaces within the oligomerization reactor to no more than 10 grams of polymer byproduct per kilogram of desired oligomerization product; the alpha-olefin comprises ethylene; the desired oligomerization product comprises 1-hexene, 1-octene, 1-decene, or a combination thereof; the polymer byproduct comprises a polyethylene (co)polymer; the diluent is selected from the group consisting of one or more $C_3$-$C_8$ linear, branched, and/or cyclic hydrocarbons; and the polymer anti-foulant reduces and/or inhibits fouling in the oligomerization reactor by at least 10% over a selective oligomerization with substantially no added polymer anti-foulant.

Embodiment 16. A method for polymerizing a polyethylene copolymer comprising contacting ethylene and an olefin oligomer product made according to the method of any of the previous embodiments in a polymerization reactor under conditions sufficient to form a polyethylene copolymer.

EXAMPLES

Many catalyst systems have been developed to oligomerize ethylene into linear alpha olefins with higher commercial value. For example, a method for the efficient production of 1-hexene from the trimerization of ethylene has been described in U.S. Pat. No. 7,425,661. Under most relevant process conditions, the olefins produced may be in liquid phase or gas phase. These flowable products are relatively easy to process. However, many catalyst systems also produce a small amount of solid polymer byproduct, which can lead to significant problems. Polymer accumulation in the reactor inlet and outlet can reduce the ability to flow the products and can eventually render the reactor system totally inoperable. In a commercial setting, periodic shutdowns would be required to clean accumulated solids from the reactor and the attached tubing. a relatively high frequency of shutdowns would have a significant impact on the overall efficiency. A faster buildup of solid material would lead to more frequent shutdowns and, therefore, a less efficient process.

While these methods described herein do not necessarily reduce the total amount of polymer byproduct formed during the oligomerization reaction, they preferably make the polymer byproduct that is formed easier to handle. The polymer byproduct made in this type of oligomerization reaction can be broken down into three types: soluble, slurry and fouling. "Soluble polymer" can form a relatively miscible solution with the reactor contents and can therefore readily flow out of the reactor. "Slurry polymer" typically does not go into solution, but also does not deposit on the reactor surfaces and thus tends to flow harmlessly out of the reactor as part of the gas-liquid-solid mixture. "Fouling polymer" deposits on the reactor walls (surfaces) as well as reactor internals, such as the baffle and the mixing impeller. This fouling polymer is the most detrimental to the efficiency of the system.

Examples 1-5

For these Examples, the polymer anti-foulant used was high density polyethylene (HDPE) granules with an average particle diameter between about 500 microns and 1 mm. These granules are available commercially; however, for the purposes of this study, they were fabricated using the following method.

The granule fabrication procedure took place in a 1-liter autoclave reactor. The reactor was first treated with scavenger and half filled with isopentane. The reactor was then brought to at temperature of about 80° C. and pressurized with ethylene to about 160 psi (1.10 MPa). Catalyst was prepared by adding about 198.8 mg of supported (PrCp)$_2$ZrCl$_2$ on silica with approximately 3 ml of heptane to a catalyst injection tube. The catalyst was injected using ethylene at about 180 psi (1.24 MPa). The reaction was then allowed to proceed for about 45 minutes with the temperature controlled to about 80° C. At the conclusion of the reaction, the ethylene was vented off and the reactor was allowed to cool before collecting the fabricated HDPE granules. The HDPE granules made in this instance were later characterized and found to have an average particle diameter of about 635 microns (HDPE "A").

The ethylene oligomerization reactions were also run in a 1-liter autoclave reactor. An ethylene trimerization catalyst, identified herein as A29, was used for the purposes of this study. The details of this catalyst system have been described in U.S. Pat. No. 7,425,661. The detailed procedure of the oligomerization reactions is described below.

Experiments were carried out in a 1-liter batch reactor with a mechanical agitator. In experiments that utilized the inert solid granules, these granules were added to the reactor first. After closing the head of the reactor, it was heated to about 80° C. using a steam jacket and was purged with nitrogen for about 1 hour to remove any catalyst poisons. The reactor was then allowed to cool to about room temperature (~20-25° C.) and was filled with about 500 ml of liquid isopentane. The agitator on the reactor was brought to about 1000 rpm. The reactor was brought to a temperature of about 85° C. and pressurized to about 430 psi (3.0 MPa) with ethylene. The catalyst and activator solutions were prepared in an injection tube and attached to the reactor. The details of the catalyst preparation procedure are described in U.S. Pat. No. 7,425,661. The catalyst and activator were pushed into the reactor with ethylene at about 450 psi (3.1 MPa). After introducing the catalyst, ethylene was fed to the reactor on pressure demand, and the reactor temperature was controlled to about 85° C. during the duration of the reaction. After about one hour, the ethylene flow was stopped and the reactor was allowed to cool to approximately room temperature. After the reactor cooled to about room temperature, the head was removed so that the products could be recovered and weighed.

Five batch reactions were carried out using the above procedure; however in two of the reactions, HDPE granules were added to the reactor at the start of the reaction. In order to assess the level of fouling polymer in each case, the polymer byproduct produced with each reaction was separated and weighed. As part of the weighing procedure, the post-reaction solid-liquid mixture was dumped from the reactor and filtered. Polymer that flowed out of the reactor, but was caught on the filter, was classified as slurry polymer. The liquid that passed through the filter was allowed to evaporate off, leaving behind the dissolved polymer. Once completely dried, this polymer was weighed and classified as solution polymer. The polymer that remained inside the reactor after the initial dump was classified as fouling polymer. The reactor agitator and baffle were removable and could be weighed before and after the reaction to determine the amount of deposition on these structures. Polymer byproduct deposited directed directly to the reactor walls was manually scraped off. The weight of fouling polymer was measured to be the sum of the weights collected from the baffle, the impeller, and the reactor walls.

The results of these experiments are summarized in Table 1. It was assumed that all of the HDPE granules poured out of the reactor and were caught on the filter paper. Therefore, the weight of HDPE granules was subtracted from the actual measured slurry weight to get the weight of new polymer formed during the reaction. The weights presented in Table 1 for slurry polymer have already had the HDPE granule weight subtracted.

a polymer byproduct oligomerization reaction content of at least about 1.0% by weight of the (non-diluent) product effluent, whereas Examples 4-5 showed a content of about 0.9% by weight or less.

Without being bound by theory, it is believed that the added polymer anti-foulant particles may reduce and/or inhibit fouling by one of two mechanisms by interacting with polymer byproduct formed during the oligomerization reaction. One proposed mechanism involves the polymer anti-foulant particles remaining in the reactor as slurry polymer and, through attractive interactions, inducing a significant proportion of the polymer byproduct that would normally end up as fouling polymer to agglomerate with the anti-foulant particles into the slurry polymer phase, which can be easily filtered. Another proposed mechanism involves the polymer anti-foulant particles remaining in the reactor as slurry polymer and, through repulsive interactions and/or saturation of the slurry phase, inducing a significant proportion of the already-solvated polymer byproduct that would normally end up as slurry and/or fouling polymer instead to solublize in the solvent/diluent and/or to remain in the solution phase, which can easily pass through the system to be removed at a later stage.

Preferably, the composition of the polymer anti-foulant can include substantially no compounds/moieties that poison the oligomerization catalyst (e.g., comprising moieties involving reactive oxygen, nitrogen, phosphorus, sulfur, or the like, or combinations thereof), or at least can include levels of such compounds/moieties low enough not to substantially poison, retard, or adversely affect the oligomerization reaction.

Examples 6-11

In order to further refine this method, a second HDPE granule batch was made using the same procedure described previously. However, in an effort to increase the granule size, the catalyst amount was lowered to about 99.4 mg and the length of the reaction was increased to about 57 minutes. All other aspects of the HDPE granule fabrication procedure were maintained similar to that used in Examples 4-5. The granules made in this batch were later characterized and found to have an average particle diameter of about 813 microns. These HDPE granules will be referred to as HDPE "B".

Six additional experiments were conducted using HDPE "B" using the same ethylene oligomerization procedure described previously. Examples 9-11 used about 5 grams of HDPE "B," while Examples 6-8 used about 10 grams of HDPE "B". The results are shown below in Table 2 below. As with the first set of experiments, all HDPE granules were assumed to all come out during filtration with the slurry polymer. The weights reported for slurry polymer in Table 2

TABLE 1

Polymer weights with and without HDPE anti-foulant.

| Example | 1-hexene formed (moles) | Fouling Polymer | Slurry Polymer | Solution Polymer |
| --- | --- | --- | --- | --- |
| 1 (no HDPE) | 1.08 | 1.70 grams | 0.21 grams | 1.78 grams |
| 2 (no HDPE) | 0.99 | 0.83 grams | 0.09 grams | 0.84 grams |
| 3 (no HDPE) | 1.28 | 1.19 grams | 0.04 grams | 1.02 grams |
| 4 (10 g HDPE "A") | 0.44 | 0.36 grams | 1.44 grams | 1.35 grams |
| 5 (10 g HDPE "A") | 0.92 | 0.12 grams | 0.98 grams | 1.01 grams |

The amount of Fouling Polymer is noticeably less in Examples 4-5, which utilized the HDPE anti-foulant, than in Examples 1-3, which did not. Indeed, Examples 1-3 showed below have already had the weight of HDPE granules subtracted from the actual measured weight. In Example 8, this approach leads to negative value for the weight of polymer.

This negative value does not mean that polymer was destroyed, but instead indicates instead that some portion of the polymer anti-foulant particles migrated into either the fouling polymer or solution polymer categories, instead of staying as 100% slurry polymer, as previously assumed.

Examples 6-11 show reduction in the amount of fouling polymer for all amounts and types of HDPE granules employed. The anti-fouling effects also appear to be enhanced as the amount of HDPE is increased from about 5 grams to about 10 grams. The anti-fouling effects also appear to be enhanced, though in a more moderate comparison, as the average particle size is decreased from about 813 microns (HDPE "B") to about 635 microns (HDPE "A").

TABLE 2

Polymer weights with varying amounts of HDPE anti-foulant.

| Example | Fouling Polymer | Slurry Polymer | Solution Polymer |
|---|---|---|---|
| 6 (10 g HDPE "B") | 0.28 grams | 1.62 grams | 2.58 grams |
| 7 (10 g HDPE "B") | 0.37 grams | 2.69 grams | 0.56 grams |
| 8 (10 g HDPE "B") | 0.30 grams | −0.13 grams | 0.21 grams |
| 9 (5 g HDPE "B") | 0.77 grams | 2.55 grams | 0.71 grams |
| 10 (5 g HDPE "B") | 0.35 grams | 1.29 grams | 1.43 grams |
| 11 (5 g HDPE "B") | 0.20 grams | 0.07 grams | 0.73 grams |

It is also noteworthy that non-polymeric (silicon carbide) anti-foulant and LDPE anti-foulant (HA 2454, available from DuPont Polymer Powders Switzerland, and having an average particle size of about 12-22 microns) both tended to undesirably and drastically increase fouling polymer under oligomerization reaction conditions similar to Examples 4-11.

It should be appreciated by one of ordinary skill in the art that any embodiments, though listed separately, may additionally or alternately be combined together within the scope of the invention to the extent that such combinations are not expressly mutually exclusive.

All documents described herein are incorporated by reference herein in their entirety, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby.

What is claimed is:

1. A method for oligomerizing olefins comprising:
   contacting, in an oligomerization reactor under oligomerization conditions, a feed comprising an alpha-olefin, a catalyst having an olefin selectivity of at least 90 mol % to a desired oligomerization product, and optionally a diluent;
   producing an effluent comprising the desired oligomerization product, unreacted olefin, and polymer byproduct having at least 50 mol % of its repeat units based on the alpha-olefin and which causes fouling on one or more surfaces within the oligomerization reactor; and
   adding a polyethylene homopolymer or copolymer anti-foulant to the oligomerization reactor.

2. The method of claim 1, wherein the anti-foulant is added in an amount sufficient to (i) limit fouling on the one or more surfaces within the oligomerization reactor to no more than 20 grams of polymer byproduct per kilogram of desired oligomerization product, (ii) remediate, per kilogram of desired oligomerization product, at least 3 grams of polymer byproduct that has fouled on the one or more surfaces within the oligomerization reactor, or (iii) both (i) and (ii).

3. The method of claim 1, further comprising the step of separating the desired oligomerization product from the effluent to attain an olefinic purity of desired oligomerization product of at least 98 mol %.

4. The method of claim 1, wherein the catalyst comprises the combination of:

a) a ligand represented by the formula:

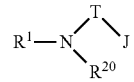

wherein:

N is nitrogen;

$R^1$ and $R^{20}$ are each independently selected from the group consisting of hydrogen, optionally substituted hydrocarbyl, heteroatom containing hydrocarbyl, and silyl, provided that $R^1$ or $R^{20}$ do not equal T-J, or alternately $R^1$ and $R^{20}$ are each independently a ring having from 4 to 8 atoms in the ring selected from the group consisting of substituted cycloalkyl, heterocycloalkyl, aryl, and heteroaryl;

T is a bridging group, preferably represented by the formula -(T'$R^2R^3$)—, where T' is carbon or silicon, $R^2$ and $R^3$ are each independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3 to 50 non-hydrogen atoms; and J is an optionally substituted six-membered heterocycle, containing at least one nitrogen atom as part of the ring, or J is an optionally substituted five-membered heterocycle, containing at least one nitrogen atom as part of the ring;

b) a metal precursor compound characterized by the general formula Cr(L)$_n$ where each L is independently selected from the group consisting of halide, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers, and combinations thereof, wherein two or more L groups may be combined in a ring structure having from 3 to 50 non-hydrogen atoms; and n is 1, 2, 3, 4, 5, or 6; and c) optionally, one or more activators.

5. The method of claim 1, wherein the feed comprises greater than about 99 wt % ethylene.

6. The method of claim 4, wherein the ligand of the catalyst is represented by at least one of the following formulas:

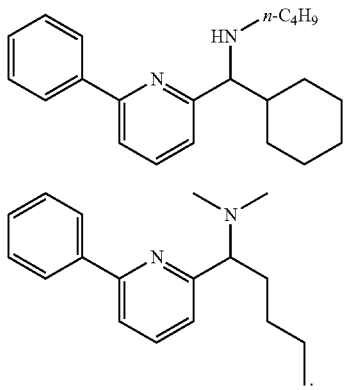

A29

A53

7. The method of claim 1, wherein the diluent is present and is selected from the group consisting of 1-butene, 1-hexene, 1-octene, toluene, propane, butane, isobutane, pentane, isopentane, and combinations thereof.

8. The method of claim 1, wherein the oligomerization conditions comprise a reaction temperature from about 60° C. to about 150° C., a reaction pressure from about 300 psi (21.1 kg/cm$^2$) to about 900 psi (63.3 kg/cm$^2$), and a reaction residence time from about 30 minutes to about 4 hours.

9. The method of claim 1, wherein the desired oligomerization product is selected from the group consisting of 1-butene, 1-hexene, 1-octene, 1-decene, and mixtures thereof.

10. The method of claim 9, wherein the catalyst has an olefin selectivity of at least 95 mol % to the desired oligomerization product.

11. The method of claim 9, wherein the catalyst has an olefin selectivity of at least 97 mol % to the desired oligomerization product.

12. The method of claim 9, wherein the catalyst has an olefin selectivity of at least 95 mol % to the desired oligomerization product, which is two olefins selected from the group consisting of 1-butene, 1-hexene, 1-octene, and 1-decene.

13. The method of claim 1, wherein one or more of the following are satisfied:
the anti-foulant has a density of at least about 0.921 g/cm$^3$;
the anti-foulant has an average particle size, $d_{50}$, of at least about 100 microns;
the anti-foulant comprises a polyethylene homopolymer or a polyethylene copolymer having less than about 6 wt % comonomer repeat units;
the amount of anti-foulant is sufficient to limit fouling on the one or more surfaces within the oligomerization reactor to no more than 10 grams of polymer byproduct per kilogram of desired oligomerization product;
the alpha-olefin comprises ethylene;
the desired oligomerization product comprises 1-hexene, 1-octene, 1-decene, or a combination thereof;
the polymer byproduct comprises a polyethylene (co)polymer;
the diluent is selected from the group consisting of one or more C$_3$-C$_8$ linear, branched, and/or cyclic hydrocarbons; and
the anti-foulant reduces and/or inhibits fouling in the oligomerization reactor by at least 10% over a selective oligomerization with substantially no added anti-foulant.

14. A method for polymerizing a polyethylene copolymer comprising
contacting, in an oligomerization reactor under oligomerization conditions, a feed comprising an alpha-olefin, a catalyst having an olefin selectivity of at least 90 mol % to a desired oligomerization product, and optionally a diluent;
adding a polyethylene homopolymer or copolymer anti-foulant to the oligomerization reactor;
producing an effluent comprising the desired oligomerization product, unreacted olefin, and polymer byproduct having at least 50 mol % of its repeat units based on the alpha-olefin and which causes fouling on one or more surfaces within the oligomerization reactor; and
contacting ethylene and the desired oligomerization product in a polymerization reactor under conditions sufficient to form a polyethylene copolymer.

15. A method for reducing and/or inhibiting polymeric fouling in an olefin oligomerization process, the method comprising:
selectively oligomerizing an alpha-olefin by contacting in an oligomerization reactor a feed comprising the alpha-olefin, a polyethylene homopolymer or copolymer anti-foulant, optionally a diluent, and a catalyst having an olefin selectivity of at least 90 mol % to a desired oligomerization product under reaction conditions sufficient to produce an effluent comprising the desired oligomerization product, unreacted olefin, and reaction byproducts comprising at least a (co)polymer having at least 50 mol % of its repeat units based on the alpha-olefin, said (co)polymer causing fouling in the oligomerization reactor in the absence of the anti-foulant, wherein the selective oligomerization containing the anti-foulant reduces and/or inhibits fouling in the oligomerization reactor by at least 10% over a selective oligomerization with substantially no added anti-foulant.

16. A method for oligomerizing olefins comprising:
contacting, in an oligomerization reactor under oligomerization conditions, a feed comprising an alpha-olefin, a catalyst having an olefin selectivity of at least 90 mol % to a desired oligomerization product, and optionally a diluent;
producing an effluent comprising the desired oligomerization product, unreacted olefin, and polymer byproduct having at least 50 mol % of its repeat units based on the alpha-olefin and which causes fouling on one or more surfaces within the oligomerization reactor; and
adding an anti-foulant comprising an polyethylene homopolymer or an unmodified polyethylene copolymer having less than about 6 wt % comonomer repeat units to the oligomerization reactor.

17. The method of claim 16, wherein the anti-foulant has an average particle size, $d_{50}$, of at least about 100 microns.

* * * * *